(12) United States Patent
Morisawa et al.

(10) Patent No.: US 8,486,290 B2
(45) Date of Patent: Jul. 16, 2013

(54) ETCHING APPARATUS, ANALYSIS APPARATUS, ETCHING TREATMENT METHOD, AND ETCHING TREATMENT PROGRAM

(75) Inventors: Toshihiro Morisawa, Yokohama (JP); Daisuke Shiraishi, Hikari (JP); Satomi Inoue, Kudamatsu (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 13/144,097

(22) PCT Filed: Nov. 20, 2009

(86) PCT No.: PCT/JP2009/069682
§ 371 (c)(1),
(2), (4) Date: Aug. 10, 2011

(87) PCT Pub. No.: WO2010/106712
PCT Pub. Date: Sep. 23, 2010

(65) Prior Publication Data
US 2011/0315661 A1      Dec. 29, 2011

(30) Foreign Application Priority Data
Mar. 17, 2009   (JP) ................................. 2009-063896

(51) Int. Cl.
*G01R 31/00*       (2006.01)
(52) U.S. Cl.
USPC ................... 216/60; 216/37; 216/67; 702/95; 702/108; 702/182; 438/9; 438/16
(58) Field of Classification Search
USPC ....... 216/37, 60, 67; 702/95, 108, 182; 438/9, 438/16
See application file for complete search history.

(56) References Cited

U.S. PATENT DOCUMENTS 5,658,423 A * 8/1997 Angell et al. ..................... 438/9
5,711,843 A * 1/1998 Jahns ....................... 156/345.24

(Continued)

FOREIGN PATENT DOCUMENTS

| CN | 1479352 | 3/2004 |
|---|---|---|
| CN | 1743505 | 3/2006 |
| JP | 06-224098 | 8/1994 |
| JP | 09-306894 | 11/1997 |
| JP | 2001-060585 | 3/2001 |

(Continued)

OTHER PUBLICATIONS

Chinese Office Action dated Dec. 3, 2012 for Application No. 200980154428.9.

*Primary Examiner* — Nadine G Norton
*Assistant Examiner* — Maki Angadi
(74) *Attorney, Agent, or Firm* — Antonelli, Terry, Stout & Kraus, LLP.

(57) ABSTRACT

There is provided an etching apparatus in which, without setting the information of the substance and the chemical reaction, a small number of representative wavelengths can be selected from a waveform at a lot of wavelengths, and an analysis process of etching data which needs large man-hours can be eliminated to efficiently set the monitoring of the etching. The etching apparatus includes: a lot/wafer/step-depending OES-data searching/acquiring function 511 for acquiring a plurality of optical emission intensity waveforms along an etching-treatment time axis; a waveform-change-existence judgment function 521 for judging the existence of the change of the plurality of light emission intensity waveforms; a waveform-correlation-matrix calculating function 522 for calculating a correlation matrix between the optical emission intensity waveforms; a waveform classifying function 523 for classifying the optical emission intensity waveforms into groups; and a representative-waveform selecting function 524 for selecting a representative optical emission intensity waveform from the group.

13 Claims, 22 Drawing Sheets

U.S. PATENT DOCUMENTS

| | | | |
|---|---|---|---|
| 5,877,032 A * | 3/1999 | Guinn et al. | 438/9 |
| 6,603,538 B1 * | 8/2003 | Oluseyi et al. | 356/72 |
| 6,741,944 B1 | 5/2004 | Verdeyen et al. | |
| 6,952,657 B2 * | 10/2005 | Jahns et al. | 702/182 |
| 2002/0119660 A1 | 8/2002 | Sarfaty et al. | |
| 2003/0136511 A1 | 7/2003 | Balasubramhanya et al. | |
| 2007/0162172 A1 | 7/2007 | Tanaka et al. | |
| 2009/0120580 A1 | 5/2009 | Kagoshima et al. | |

FOREIGN PATENT DOCUMENTS

| | | |
|---|---|---|
| JP | 2001-244254 | 9/2001 |
| JP | 2001-521280 | 11/2001 |
| JP | 2003-017471 | 1/2003 |
| JP | 2005-217448 | 8/2005 |
| JP | 2005-340547 | 12/2005 |
| JP | 2006-317371 | 11/2006 |
| JP | 2007-227969 | 9/2007 |

* cited by examiner

FIG. 2

<CAUSE OF CORRELATION OF OPTICAL EMISSION INTENSITY>

201 — ■ FIRST ORDER SYSTEM [A]→[B]+[C]

$$202 \quad \frac{d[A]}{dt} = k[A] \rightarrow [A] = ae^{-kt} + b$$

203 — ■ SECOND ORDER SYSTEM 2[A] →[C]

$$204 \quad \frac{d[A]}{dt} = k[A]^2 \rightarrow [A] = a - \frac{1}{k}\frac{1}{t-b}$$

IN CHEMICAL REACTION, CORRELATION IS NATURALLY ESTABLISHED

205 — ■ HIGH ORDER SYSTEM [A]+···→[C]

$$206 \quad [A] = a - \frac{1}{k}\frac{1}{(t-b)^n}$$

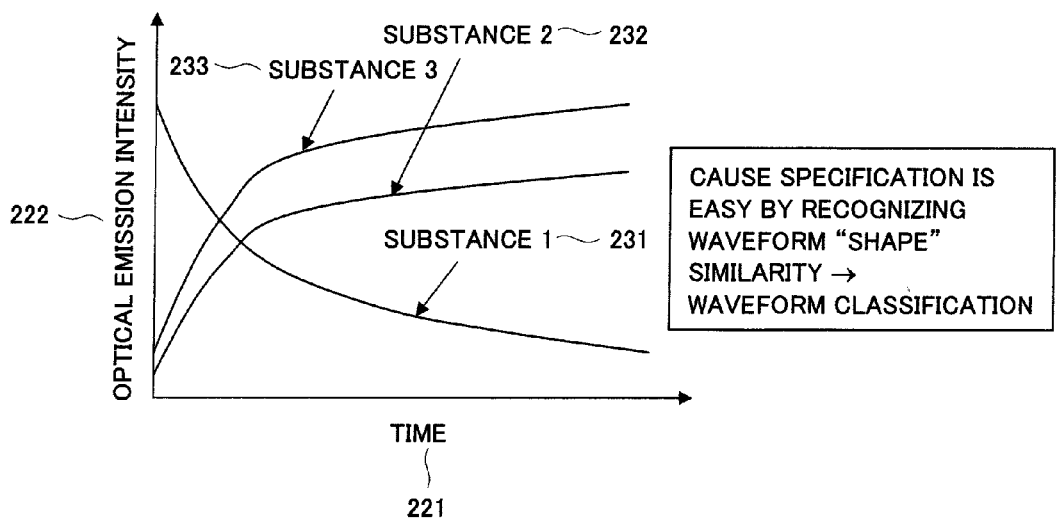

[SUBSTANCE 1]→[SUBSTANCE 2]+[SUBSTANCE 3] — 211

CAUSE SPECIFICATION IS EASY BY RECOGNIZING WAVEFORM "SHAPE" SIMILARITY → WAVEFORM CLASSIFICATION

FIG. 3A
WAVEFORM GRAPH

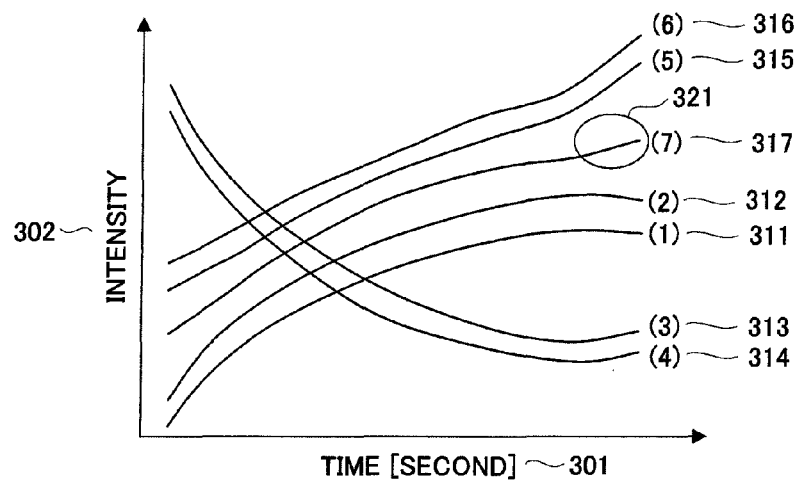

FIG. 3B
RESULT OF PRINCIPAL COMPONENT ANALYSIS

INFLUENCE 86%    INFLUENCE 13%

|  | FIRST PRINCIPAL COMPONENT | SECOND PRINCIPAL COMPONENT | THIRD PRINCIPAL COMPONENT |
|---|---|---|---|
| EIGEN VALUE | 23.2274 | 3.6256 | 0.1068 |
| CUMULATIVE CONTRIBUTION RATIO | 86.0% | 99.5% | 99.9% |

EIGEN VECTOR

| WAVEFORM | FIRST PRINCIPAL COMPONENT | SECOND PRINCIPAL COMPONENT | THIRD PRINCIPAL COMPONENT |
|---|---|---|---|
| (1) | 0.4140 | 0.1048 | 0.6550 |
| (2) | 0.4112 | 0.1513 | 0.5708 |
| (3) | −0.4039 | −0.2267 | 0.2061 |
| (4) | −0.3991 | −0.2629 | −0.0778 |
| (5) | 0.3357 | −0.5299 | −0.1941 |
| (6) | 0.2902 | −0.6401 | −0.1704 |
| (7) | 0.3744 | −0.3939 | −0.3605 |

TENDENCY DETERMINATION BY POSITIVE OR NEGATIVE

| | WAVEFORM A | WAVEFORM B | WAVEFORM C | WAVEFORM D |
|---|---|---|---|---|
| CORRELATION WITH WAVEFORM A | 1 | 0 | −1 | 1 |
| CORRELATION WITH WAVEFORM B | 0 | 1 | 0 | 0 |
| CORRELATION WITH WAVEFORM C | −1 | 0 | 1 | −1 |
| CORRELATION WITH WAVEFORM D | 1 | 0 | −1 | 1 |

| | WAVEFORM A | WAVEFORM B | WAVEFORM C | WAVEFORM D |
|---|---|---|---|---|
| WAVEFORM A | 1 | 0 | −1 | 1 |
| WAVEFORM B | 0 | 1 | 0 | 0 |
| WAVEFORM C | −1 | 0 | 1 | −1 |
| WAVEFORM D | 1 | 0 | −1 | 1 |

FIG. 8

■OUTLINE OF METHOD OF CLUSTER ANALYSIS
TWO CLUSTERS HAVING THE SHORTEST DISTANCE THEREBETWEEN ARE INTEGRATED TO FORM NEW CLUSTER.
THE DISTANCE IS FURTHER SEARCHED TO ADVANCE THE CLUSTER FORMATION.

710 : <DISTANCE EVALUATION 1>

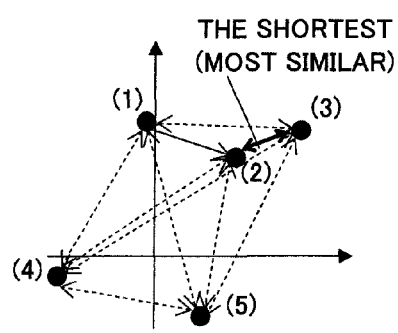

720 : <INTEGRATION 1>
721: CLUSTER FORMATION
722: GRAVITY CENTER

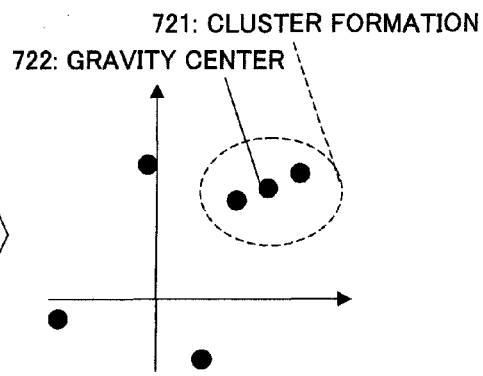

730 : <DISTANCE EVALUATION 2>

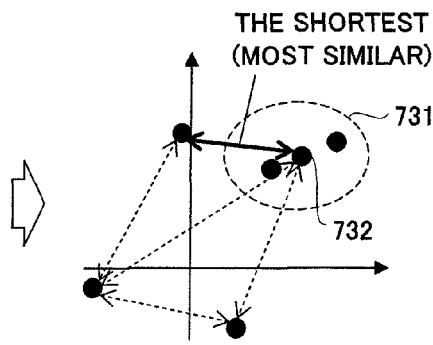

740 : <INTEGRATION 2>
743: GRAVITY CENTER

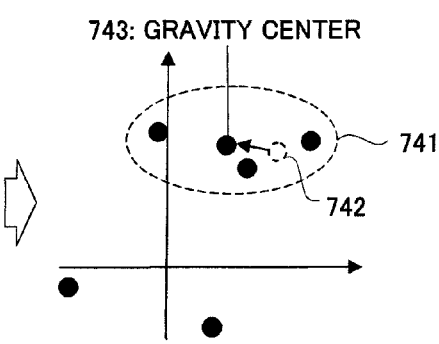

750 : <DISTANCE EVALUATION 3>

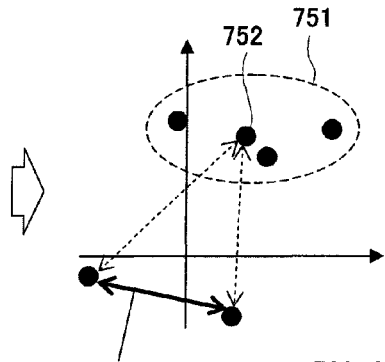

760 : <INTEGRATION 3>

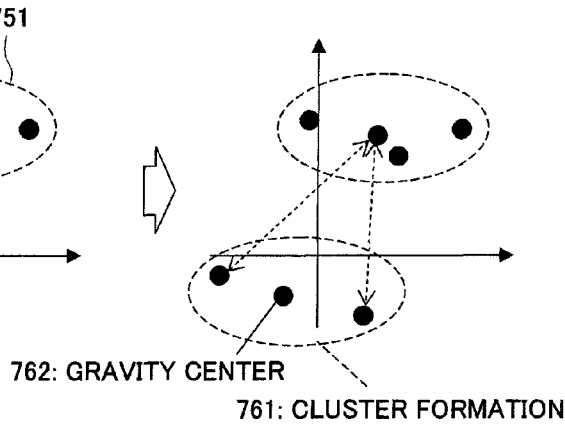

762: GRAVITY CENTER
761: CLUSTER FORMATION

FIG. 10

|  | (1) | (2) | (3) | (4) | (5) | (6) | (7) | (8) | (9) | (10) | (11) | (12) | (13) | (14) | (15) |
|---|---|---|---|---|---|---|---|---|---|---|---|---|---|---|---|
| (1) | 1 | −1 | −1 | −1 | −1 | 0.56 | −0.9 | 0.21 | 0.62 | 0.97 | 0.95 | 0.98 | 0.99 | 0.99 | 1 |
| (2) | −1 | 1 | 0.98 | 0.98 | 0.98 | −0.4 | 0.93 | −0.1 | −0.5 | −0.9 | −0.9 | −0.9 | −0.9 | −0.9 | −0.9 |
| (3) | −1 | 0.98 | 1 | 1 | 1 | −0.5 | 0.93 | −0.1 | −0.5 | −1 | −0.9 | −1 | −1 | −1 | −1 |
| (4) | −1 | 0.98 | 1 | 1 | 1 | −0.5 | 0.93 | −0.1 | −0.6 | −1 | −0.9 | −1 | −1 | −1 | −1 |
| (5) | −1 | 0.98 | 1 | 1 | 1 | −0.5 | 0.95 | −0.1 | −0.5 | −1 | −0.9 | −1 | −1 | −1 | −1 |
| (6) | 0.56 | −0.4 | −0.5 | −0.5 | −0.5 | 1 | −0.1 | 0.92 | 0.99 | 0.73 | 0.78 | 0.7 | 0.65 | 0.66 | 0.62 |
| (7) | −0.9 | 0.93 | 0.93 | 0.93 | 0.95 | −0.1 | 1 | 0.24 | −0.2 | −0.8 | −0.7 | −0.8 | −0.8 | −0.8 | −0.9 |
| (8) | 0.21 | −0.1 | −0.1 | −0.1 | −0.1 | 0.92 | 0.24 | 1 | 0.89 | 0.42 | 0.49 | 0.37 | 0.31 | 0.33 | 0.28 |
| (9) | 0.62 | −0.5 | −0.5 | −0.6 | −0.5 | 0.99 | −0.2 | 0.89 | 1 | 0.78 | 0.83 | 0.75 | 0.7 | 0.71 | 0.68 |
| (10) | 0.97 | −0.9 | −1 | −1 | −0.9 | 0.73 | −0.8 | 0.42 | 0.78 | 1 | 1 | 1 | 0.99 | 0.99 | 0.99 |
| (11) | 0.95 | −0.9 | −0.9 | −0.9 | −0.9 | 0.78 | −0.7 | 0.49 | 0.83 | 1 | 1 | 0.99 | 0.98 | 0.98 | 0.97 |
| (12) | 0.98 | −0.9 | −1 | −1 | −1 | 0.7 | −0.8 | 0.37 | 0.75 | 1 | 0.99 | 1 | 1 | 1 | 1 |
| (13) | 0.99 | −0.9 | −1 | −1 | −1 | 0.65 | −0.8 | 0.31 | 0.7 | 0.99 | 0.98 | 1 | 1 | 1 | 1 |
| (14) | 0.99 | −0.9 | −1 | −1 | −1 | 0.66 | −0.8 | 0.33 | 0.71 | 0.99 | 0.98 | 1 | 1 | 1 | 1 |
| (15) | 1 | −0.9 | −1 | −1 | −1 | 0.62 | −0.9 | 0.28 | 0.68 | 0.99 | 0.97 | 1 | 1 | 1 | 1 |

GROUP 1

|      | (1)   | (10)  | (11)  | (12)  | (13)  | (14)  | (15)  |
|------|-------|-------|-------|-------|-------|-------|-------|
| (1)  | 1     | 0.975 | 0.953 | 0.984 | 0.994 | 0.990 | 0.996 |
| (10) | 0.975 | 1     | 0.996 | 0.998 | 0.993 | 0.995 | 0.990 |
| (11) | 0.953 | 0.996 | 1     | 0.991 | 0.980 | 0.983 | 0.974 |
| (12) | 0.984 | 0.998 | 0.991 | 1     | 0.997 | 0.998 | 0.995 |
| (13) | 0.994 | 0.993 | 0.980 | 0.997 | 1     | 0.999 | 0.999 |
| (14) | 0.990 | 0.995 | 0.983 | 0.998 | 0.999 | 1     | 0.998 |
| (15) | 0.996 | 0.990 | 0.974 | 0.995 | 0.999 | 0.998 | 1     |
| AVERAGE | 0.982 | 0.991 | 0.979 | 0.994 | 0.994 | 0.994 | 0.992 |

↑ MAXIMUM

GROUP 2

|      | (6)   | (8)   | (9)   |
|------|-------|-------|-------|
| (6)  | 1     | 0.922 | 0.993 |
| (8)  | 0.922 | 1     | 0.891 |
| (9)  | 0.993 | 0.891 | 1     |
| AVERAGE | 0.958 | 0.907 | 0.942 |

↑ MAXIMUM

GROUP 3

|      | (2)   | (3)   | (4)   | (5)   | (7)   |
|------|-------|-------|-------|-------|-------|
| (2)  | 1     | 0.984 | 0.983 | 0.980 | 0.928 |
| (3)  | 0.984 | 1     | 1.000 | 0.999 | 0.933 |
| (4)  | 0.983 | 1.000 | 1     | 0.999 | 0.931 |
| (5)  | 0.980 | 0.999 | 0.999 | 1     | 0.946 |
| (7)  | 0.928 | 0.933 | 0.931 | 0.946 | 1     |
| AVERAGE | 0.969 | 0.979 | 0.978 | 0.981 | 0.934 |

↑ MAXIMUM

FIG. 15

| | (1) | (2) | (3) | (4) | (5) | (6) | (7) | (8) |
|---|---|---|---|---|---|---|---|---|
| (1) | 1 | 0.999 | 0.992 | 0.936 | 0.885 | 0.919 | 0.938 | 0.841 |
| (2) | 0.999 | 1 | 0.991 | 0.938 | 0.882 | 0.917 | 0.936 | 0.838 |
| (3) | 0.992 | 0.991 | 1 | 0.972 | 0.902 | 0.939 | 0.952 | 0.862 |
| (4) | 0.936 | 0.938 | 0.972 | 1 | 0.901 | 0.938 | 0.939 | 0.867 |
| (5) | 0.885 | 0.882 | 0.902 | 0.901 | 1 | 0.986 | 0.979 | 0.993 |
| (6) | 0.919 | 0.917 | 0.939 | 0.938 | 0.986 | 1 | 0.997 | 0.975 |
| (7) | 0.938 | 0.936 | 0.952 | 0.939 | 0.979 | 0.997 | 1 | 0.964 |
| (8) | 0.841 | 0.838 | 0.862 | 0.867 | 0.993 | 0.975 | 0.964 | 1 |

1401

FIG. 19
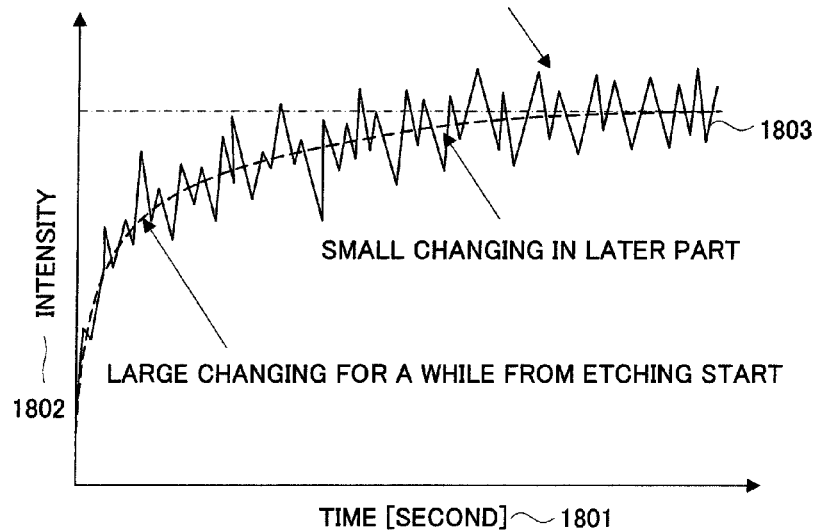
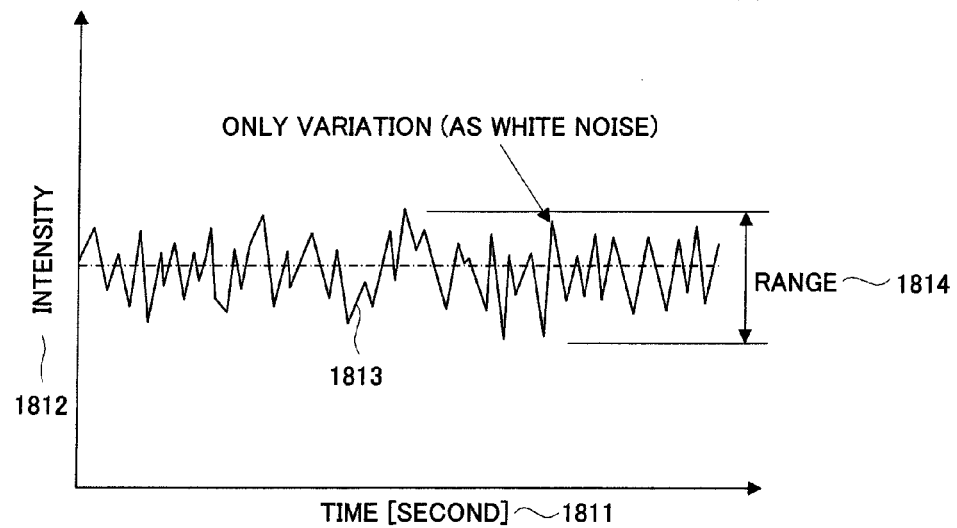

ETCHING APPARATUS, ANALYSIS APPARATUS, ETCHING TREATMENT METHOD, AND ETCHING TREATMENT PROGRAM

TECHNICAL FIELD

The present invention relates to, in an etching apparatus and an analysis apparatus monitoring optical emission of plasma in the etching apparatus, a method of classifying a waveform of optical emission intensity during an etching treatment to select a waveform affecting a result of the etching treatment. More particularly, the present invention relates to a method of classifying a wavelength based on a shape similarity of the waveform to select a representative wavelength and a method of quantitatively judging a waveform having small change.

BACKGROUND ART

In order to obtain a fine shape of a semiconductor device formed on a wafer or others, an etching treatment of ionizing and dissociating substances by using plasma and removing the substances on the wafer by an action (reaction on a surface of the wafer) of the substances is performed. The ionized substances and dissociated substances (radicals) are various, and the substances on the wafer are also various types in accordance with product functions.

Further, in order to form the shape on the wafer, the etching treatment is performed after coating a resist made of an organic-based substance and forming the shape by photolithography. Also, in order to obtain a predetermined shape, a substance for adjusting a reaction speed is also introduced. In a chamber container in which the etching treatment is performed, various types of substances are reacted with each other.

The ionization and dissociation phenomenon caused by the plasma results in a luminous phenomenon, and therefore, an optical emission spectroscopy (OES) is mounted on an etching apparatus of performing the treatment by using the plasma to monitor the generation state of the plasma.

Conventionally, a method of extracting the substances affecting the reaction and the change of optical emission from the OES data is described in Japanese Patent Application Laid-Open Publication No. H06-224098 (Patent Document 1), Japanese Patent Application Laid-Open Publication No. 2001-60585 (Patent Document 2), Japanese Patent Application Laid-Open Publication No. 2001-244254 (Patent Document 3), Japanese Patent Application Laid-Open Publication No. 2003-17471 (Patent Document 4), Japanese Patent Application Laid-Open Publication No. 2005-340547 (Patent Document 5), Japanese Patent Application Laid-Open Publication No. H09-306894 (Patent Document 6), and Japanese Patent Application Laid-Open Publication (Translation of PCT Application) No. 2001-521280 (Patent Document 7).

Patent Document 1 describes a method of acquiring optical emission spectrum (OES) from the plasma in the chamber, specifying the substances in the chamber on real time based on information of spectrum lines corresponding to the substances, and judging a relative concentration level of the substance.

Patent Document 2 describes a method of performing principal component analysis by using a correlation coefficient of an optical emission waveform, and comparing a referenced principal component with a principal component obtained upon execution of manufacturing to specify a principal component affecting processes and a state of a chamber, so as to, for example, control to detect an end point.

Patent Document 3 describes a method of performing a principal component analysis by using a correlation coefficient of an optical emission waveform, and comparing a referenced principal component with a principal component obtained upon execution of manufacturing similarly to Patent Document 2. Patent document 3 describes a method of not directly monitoring optical emission spectrum of plasma but targeting the reflected optical emission intensity on a wafer surface with having plasma optical emission as a light source to control a film thickness.

Patent Document 4 describes a method of modeling a relation between a monitoring result of a process volume during a treatment such as OES and a process treatment result, and obtaining an optimal recipe, so as to control plasma treatment. More particularly, Patent document 4 describes to perform principal component analysis for an OES data and extract a wavelength forming a large-changed waveform.

Patent Document 5 describes a method, particularly for end point detection, of previously preparing patterns of waveform changes in a database, and detecting the end point in accordance with the patterns when the patterns are matched with a specific pattern during an etching treatment. The patterns are based on three types of upward, downward, and flat patterns, and besides, are set in detail depending on a degree of the change.

Patent Document 6 describes a method of dispersing plasma optical emission with connecting a plasma treatment apparatus, detecting and analyzing time change of an intensity for each waveform, so as to automatically determine an optimal wavelength.

Patent Document 7 describes a method of monitoring each magnitude of P pieces of radiation wavelengths along treatment time to create a correlation existing among the radiation wavelengths, comparing with a previous plasma treatment, and detecting its state.

PRIOR ART DOCUMENTS

Patent Documents

Patent Document 1: Japanese Patent Application Laid-Open Publication No. H06-224098
Patent Document 2: Japanese Patent Application Laid-Open Publication No. 2001-60585
Patent Document 3: Japanese Patent Application Laid-Open Publication No. 2001-244254
Patent Document 4: Japanese Patent Application Laid-Open Publication No. 2003-17471
Patent Document 5: Japanese Patent Application Laid-Open Publication No. 2005-340547
Patent Document 6: Japanese Patent Application Laid-Open Publication No. H09-306894
Patent Document 7 (Translation of PCT Application): Japanese Patent Application Laid-Open Publication No. 2001-521280

DISCLOSURE OF THE INVENTION

Problems to be Solved by the Invention

However, in the method described in Patent Document 1, although the optical emission wavelengths can be limited by a peak of the optical emission caused by the same substance, the optical emission at a wavelength other than those of the setting information of the spectrum lines corresponding to the substances cannot be classified. Also, regarding the waveform, a method of evaluating a commonality of the waveform change is not described, and the wavelength cannot be classified based on a reaction.

Further, in the method described in Patent Document 2, although the optical emission intensity change (corresponding to waveform) which is commonly changed at all wavelength regions can be evaluated by evaluating the principal component by the principal component analysis, the wavelength cannot be classified by evaluating a partial difference in the waveform between the wavelengths.

Still further, in the method described in Patent Document 3, similarly to the method described in Patent Document 2, the waveform cannot be classified.

Still further, in the method described in Patent Document 4, the extraction of the wavelength forming the large-changed waveform by the principal component analysis is merely described, and the classification of a plurality of waveforms is not described.

Still further, in the method described in Patent Document 5, since the patterns are previously registered for classifying the change patterns, a waveform which is variously changed in accordance with a content of the etching treatment cannot be classified.

Still further, in the method described in Patent Document 6, the time change of the optical emission intensity of the plasma emission is analyzed, and a difference between the level of the optical emission intensity at a time point before the end point of the plasma treatment and the level of the optical emission intensity at a time point after the end point thereof is detected. However, only the waveform change based on a difference between two intensities can be evaluated by this method, and therefore, the method is insufficient to classify waveforms which are variously changed as different from each other.

Still further, in the method described in Patent Document 7, the correlation existing among the radiation wavelengths is created, and the end point of the etching treatment is detected based on an angle between principal-component vectors of the principal components in the correlation. However, the principal component is obtained by collecting the common change at the plurality of wavelengths, and therefore, even if the angle between the vectors is examined, existence of the common change at the plurality of wavelengths can be merely found out, and thus, the representative wavelength cannot be found out from the variously changed waveforms.

Accordingly, a preferred aim of the present invention is to provide an etching apparatus, an analysis apparatus, an etching treatment method, and an etching treatment program, which can select a small number of representative wavelengths from waveforms at a plurality of wavelengths without setting information of substances or chemical reactions, reduce analysis of etching data using large man-hours, and efficiently set to monitor the etching.

The above and other preferred aims and novel characteristics of the present invention will be apparent from the description of the present specification and the accompanying drawings.

Means for Solving the Problems

A summary of the typical ones of the inventions disclosed in the present application will be briefly described as follows.

That is, as the summary of the typical one, a calculator system includes: an optical-emission intensity waveform acquiring means for acquiring an optical-emission intensity waveform along a time axis of a plurality of etching treatments in plasma emission data obtained during the etching treatment once or more times having been performed in a past; a waveform-change-existence judging means for judging existence of change of the plurality of optical emission intensity waveforms acquired by the optical-emission intensity waveform acquiring means; a waveform correlation matrix calculating means for calculating a matrix of a correlation between optical emission intensity waveforms judged as the existence of the change by the waveform-change-existence judging means; a waveform classifying means for setting each column or each row of the correlation matrix calculated by the waveform correlation matrix calculating means to a vector corresponding to the optical emission intensity waveform, evaluating a similarity between the optical emission intensity waveforms based on a value of the vector, and classifying the optical emission intensity waveforms into groups; and a representative waveform selecting means for selecting a representative optical emission intensity waveform from the group classified by the waveform classifying means, specifying the selected representative optical emission intensity waveform as an optical emission intensity waveform affecting an etching performance or a result of the etching treatment on a wafer, determining a wavelength at which the optical emission intensity waveform is obtained as an optical emission wavelength to be monitored, and displaying its result on a terminal.

Effects of the Invention

The effects obtained by typical aspects of the present invention will be briefly described below.

That is, the effect obtained by the typical aspects is that, since an optical emission wavelength to be monitored can be automatically selected without setting information of substances or chemical reactions, the monitoring of the etching can be efficiently set to judge anomaly/normality. Also, mistakes such as judgment error for a phenomenon caused by missed registration of substances and chemical reactions or manual judgment can be prevented.

BRIEF DESCRIPTIONS OF THE DRAWINGS

FIG. 2 is an explanatory diagram for explaining a cause of a correlations in an optical emission intensity used in the etching apparatus according to the embodiment of the present invention;

FIG. 3 is a diagram showing an example of waveforms and principal component analysis result of the waveforms used in the etching apparatus according to the embodiment of the present invention;

FIG. 8 is an explanatory diagram for explaining an outline of a calculation method of the cluster analysis in the etching apparatus according to the embodiment of the present invention;

FIG. 10 is a diagram showing an example of a correlation matrix of 15 wavelengths in the etching apparatus according to the embodiment of the present invention;

FIG. 12 is a diagram showing an example of a group-depending correlation matrix of waveforms at 15 wavelengths in the etching apparatus according to the embodiment of the present invention;

FIG. 15 is a diagram showing an example of a correlation matrix between 8 waveforms at the same wavelength in the etching apparatus according to the embodiment of the present invention;

FIG. 19 is a diagram showing an example of a waveform containing variation in the etching apparatus according to the embodiment of the present invention;

BEST MODE FOR CARRYING OUT THE INVENTION

Figure 1:
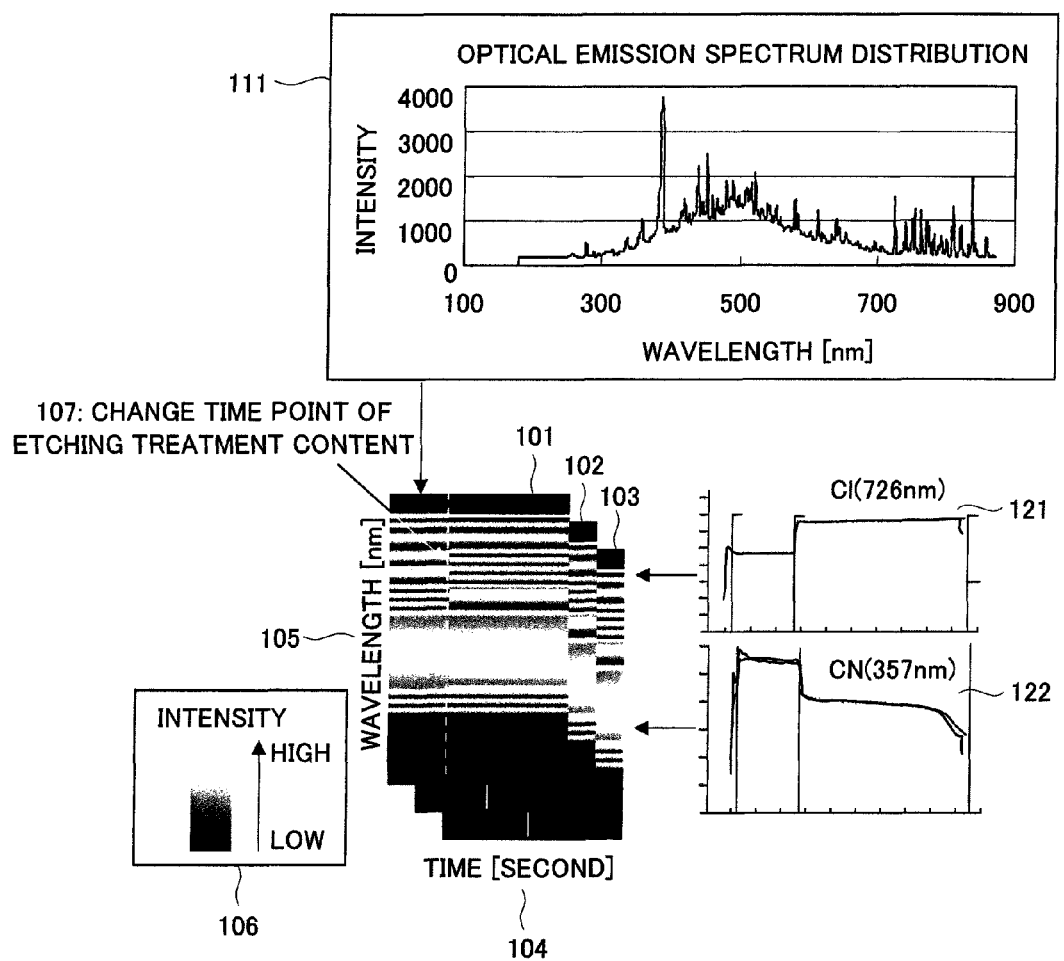
FIG. 1 is a diagram showing an example of spectra and waveforms obtained by an optical emission spectrometry OES used in an etching apparatus according to an embodiment of the present invention.

Hereinafter, embodiments of the present invention will be described in detail with reference to the accompanying drawings. Note that components having the same function are denoted by the same reference symbols throughout the drawings for describing the embodiment, and the repetitive description thereof will be omitted.

First, a summary of the present invention will be described.

In the present invention, a spectrometry (OES) is mounted on an etching apparatus and includes means for acquiring an OES data for each etching treatment. The optical emission spectrometry is connected to a storage device or a database and includes means for storing the OES data in the storage device or the database. The etching apparatus includes: means for acquiring a plurality of waveforms from the OES data, classifying the waveforms, obtaining a representative waveform, and monitoring the etching; means for judging anomaly/normality; means for analyzing/evaluating the result of the etching treatment; means for correcting an etching treatment condition; and means for acquiring the OES data from the storage device or the database for them. Note that each of these means may be included in an analysis apparatus connected to the etching apparatus, and a configuration such as observing the etching treatment by the analysis apparatus may be used.

Also, in order to judge the anomaly/normality of the etching, the etching apparatus includes: means for setting a judgment criterion; and means for storing a judgment result in the storage device or the database or displaying/notifying the result to a user.

Further, in order to correspond the etching treatment result to the correlation coefficient of the optical emission intensity or the waveform of the OES data, the etching apparatus includes: means for storing the etching treatment result in the storage device or the database; means for acquiring the etching treatment result from the storage device or the database; means for obtaining a relation between the etching treatment result and the correlation coefficient of the optical emission intensity or the waveform; and means for estimating/predicting the etching treatment result from the correlation coefficient of the optical emission intensity or the waveform.

In order to correct the etching treatment condition, the etching apparatus includes: means for setting a target etching treatment result; means for calculating a correcting amount of the etching treatment condition (etching time, gas flow rate, pressure, voltage, or temperature) based on an error between an actual etching treatment result and the target; and means for setting the obtained condition in the etching apparatus.

In the present invention, first, by a function of acquiring the waveform from the OES data and calculating/evaluating a magnitude of a change amount with respect to variation in the optical emission intensity, the existence of the waveform change or the waveform having large change is found out.

Also, by providing a function of acquiring a plurality of waveforms from the OES data obtained by performing the etching treatment once or more times, calculating a correlation matrix of the waveform, obtaining a correlation coefficient vector for each waveform, and classifying the waveform by the correlation coefficient vector of each waveform and a function of determining a representative waveform by the correlation coefficient vector for each classification, the optical emission wavelength to be automatically monitored is obtained, particularly, without using information of a relation between substances and the optical emission wavelength or a relation in chemical reaction.

Also, by a function of corresponding a relation between the etching treatment result to the relation of the optical emission intensity of the selected waveform, a criterion of the anomaly/normality of the etching is obtained to judge the anomaly/normality, and the etching treatment is analyzed/evaluated, and besides, the etching treatment condition is corrected to control the etching treatment result.

Further, by a function of obtaining a correlation coefficient with a waveform obtained by the other etching treatment based on a waveform obtained by one etching treatment and corresponding the correlation coefficient to the etching treatment result, the criterion of the anomaly/normality of the etching is obtained to judge the anomaly/normality, and the etching treatment is analyzed/evaluated, and besides, the etching treatment condition is corrected to control the etching treatment result. By a function of modeling the relation between the correlation coefficient and the etching treatment result by a mathematical equation, the etching treatment result can be estimated/predicted.

Hereinafter, a specific embodiment of each of the above-described means and the above-described functions of the present invention will be explained.

First, with reference to FIGS. 1 to 3, a basic technique and a basic treatment used in an etching apparatus according to an embodiment of the present invention will be explained. FIG. 1 is a diagram showing an example of spectra and waveforms obtained by an optical emission spectrometry OES used in the etching apparatus according to the embodiment of the present invention, FIG. 2 is an explanatory diagram for explaining a cause of the correlation of the optical emission intensity used in the etching apparatus according to the embodiment of the present invention, and FIG. 3 is a diagram showing an example of the waveform and a principal component analysis result thereof used in the etching apparatus according to the embodiment of the present invention.

First, an example of an optical emission data obtained by the optical emission spectrometry OES is shown in FIG. 1.

As shown in FIG. 1, an optical-emission intensity spectrum distribution taking time 104 on an x axis and a wavelength 105 on a y axis can be expressed as a bit map. The bit maps 101, 102, and 103 draw the luminous phenomena for a plurality of wafers.

It is found out that an optical-emission spectrum distribution 111 of optical emission intensity at a certain time point has a globally convex shape in a vicinity of a center of the monitored wavelengths and has peaks at a lot of wavelength positions. Also, from the optical emission intensity, that is waveforms 121 and 122, at a specific wavelength along treatment time, it is found out that the optical emission intensity is changed as progressing the etching treatment, and that the luminous phenomenon is changed at a point 107 when a content of the etching treatment is changed.

By monitoring the luminous phenomenon caused by plasma, a performance of the etching treatment can be confirmed. For example, upon start of the etching apparatus, the etching treatment is confirmed by judging whether a predetermined reaction is acting or not. Also, in high-volume manufacturing, the anomaly is detected by monitoring the optical emission in consecutive work of wafers, and the optical emission data is utilized for detecting the end point for determining a time point of finish of the etching treatment.

More particularly, for the optical emission data, a state of the etching can be monitored simultaneously parallely during the etching treatment, and therefore, it is important that a state of the optical emission can be efficiently determined, and that the state of the optical emission can be automatically determined every time of work of the wafer for usage in the high-volume manufacturing.

In order to performing such determination, a wavelength and an intensity of the wavelength at a position where the peak is generated in the spectra are analyzed. This is because the optical emission is observed at a specific wavelength in accordance with the substances in the chamber. However, as shown in the optical-emission spectrum distribution 111, several tens of peaks are observed, and therefore, it is difficult to specify a substance largely affecting the etching treatment. Accordingly, it is required to specify a certain substance affecting the etching performance so that the wavelength to be monitored is limited for the determination.

The etching is a chemical reaction based on a material reaction. In this reaction, one substance (molecular composition) is changed to the other substance (molecular composition), and there is naturally a high correlation in the change therebetween. A cause of the correlation in the optical emission intensity based on this reaction is as shown in FIG. 2.

In FIG. 2, in a first order system 201, a substance [A] is decomposed into [B] and [C], and a reaction process is determined by an equation 202.

In a second order system 203, two substances [A] become [C], and a reaction process is determined by an equation 204. Even in a high order system 205 in which a lot of substances become [C], a reaction process is determined by an equation 206.

That is, a relation in increase and decrease of the substances can be explained by one substance in each reaction. For example, in a reaction 211 in which [Substance 1] is changed to [Substance 2] and [Substance 3], there is a correlation between waveforms such that, Substance 2 (232) and Substance 3 (233) are correspondingly increased as decrease of Substance 1 (231).

Accordingly, the wavelength of the optical emission can be limited such that the substance to be monitored is only [Substance 1].

Further, the spectra of the optical emission have characteristics related to substance overlap. For example, one type of a substance emits light at a plurality of wavelengths such that spectrum lines of silicon fluoride SiF are appeared at wavelengths of 334.6 [nm], 336.3 [nm], 436.8 [nm], 440.1 [nm], and 777.0 [nm]. Therefore, there is also a correlation between the waveforms at these wavelengths based on a state of the substance.

Accordingly, by monitoring the wavelength of the optical emission corresponding to the substance representing the reaction based on such a correlation between the waveforms, the wavelength can be efficiently limited.

Also, the principal component analysis is an analysis method of using a correlation matrix of data between a plurality of data items to decompose a combination of the data items simultaneously changed with each other or independently changed from each other as a principal component based on the magnitude of the change. A combination of the change between the data items is obtained as a principal component (eigenvector). The magnitude of the change or an occupying rate of the principal component with respect to the overall change is obtained as a contribution rate.

An example of waveforms and results of the principal component analysis of the waveforms (up to third principal component) are as shown in FIG. 3. According to a graph of the waveforms, it is found out that there are similarities in a combination of a waveform (1) 311, a waveform (2) 312, and a waveform (7) 317 with each other, a combination of a waveform (3) 313 and a waveform (4) 314 with each other, and a combination of a waveform (5) 315 and a waveform (6) 316 with each other.

When the classification by positive and negative at each waveform of the principal components is reviewed, in a first principal component, the classification can be made such as a combination of the waveform (1) 311, the waveform (2) 312, the waveform (5) 315, the waveform (6) 316, and the waveform (7) 317 and a combination of the waveform (3) 313 and the waveform (4) 314.

This means that the waveforms can be classified into combinations of upward waveforms and downward waveforms. However, according to a second principal component, the waveforms are classified into a combination of the waveform (1) 311 and the waveform (2) 312 and a combination of the waveform (5) 315, the waveform (6) 316, and the waveform (7) 317.

This is because, due to change in a part shown by a numerical symbol 321 of FIG. 3, the waveforms are classified by a commonality of the change having a contribution rate of 13%.

Accordingly, even if it is reviewed that the classification is determined by the magnitude of the eigenvector of the first principal component, since the waveform (1) 311 and the waveform (2) 312 have very close values to each other, their changes have a high commonality. However, relations with the waveform (5) 315, the waveform (6) 316, and the waveform (7) 317 cannot be numerically determined.

In the principal component analysis, while large changes can be classified, it is difficult to quantitatively classify smaller changes, which means that the principal component analysis cannot be utilized for automatic classification.

Accordingly, in the present embodiment, first, in a plurality of waveforms of the OES data, the existence of the waveform change is determined, similar waveforms of a plurality of changing waveforms are classified based on the correlation matrix to obtain the representative waveform, and the etching treatment is monitored, so that, more particularly, the judgment of anomaly/normality of the etching, the analysis/evaluation of the etching treatment result, and the condition correction for improving an accuracy of the etching treatment result can be performed.

Note that the etching treatment result is a quantitative result obtained by inspecting a wafer to which the etching treatment is performed, and is a quantitative value of a difference in various dimensions, characteristics, numbers, or a difference before/after the etching treatment. Also, in order to determine the existence of the change in each waveform, a magnitude of the change with respect to the variation is evaluated. In this manner, the existence of the waveform change containing the variation can be quantitatively determined.

Figure 4:
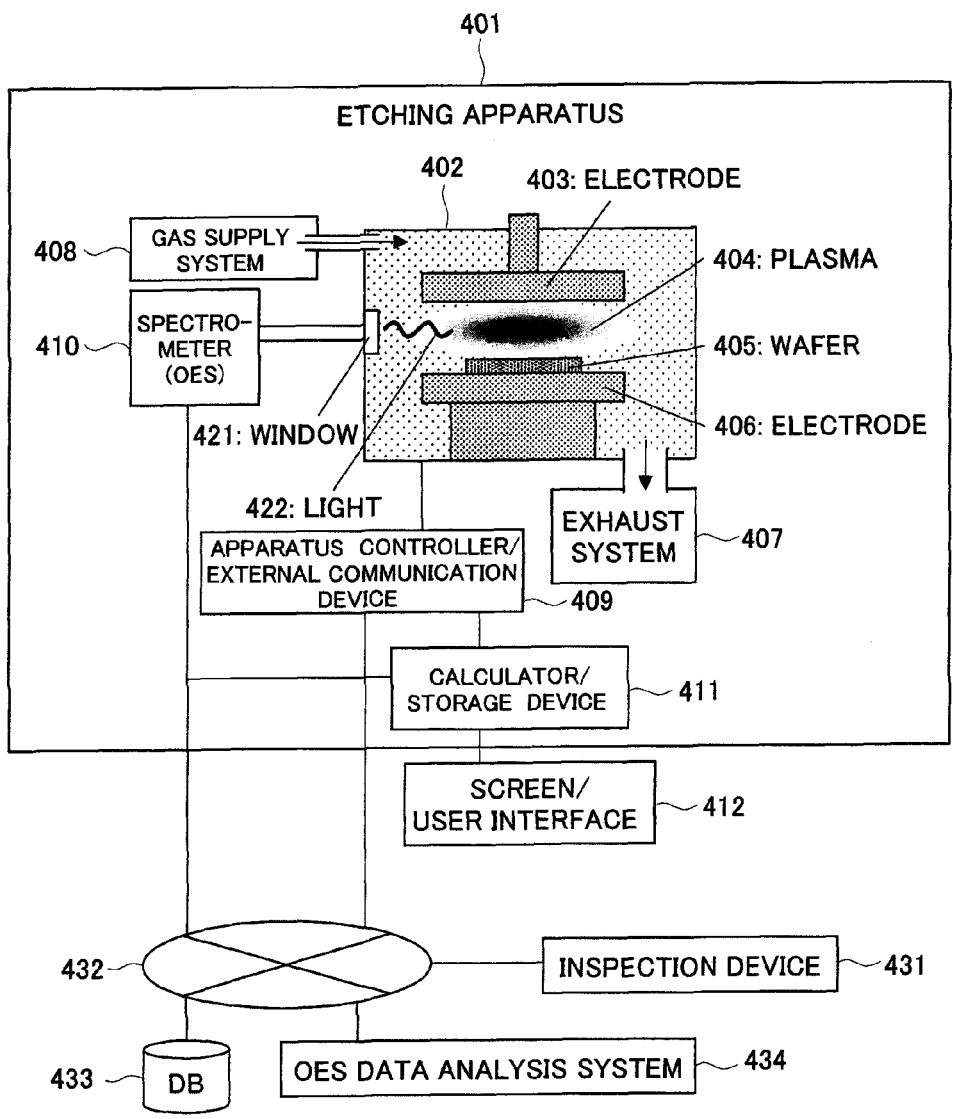
FIG. 4 is a schematic diagram showing a configuration of the etching apparatus according to the embodiment of the present invention.
Figure 5:
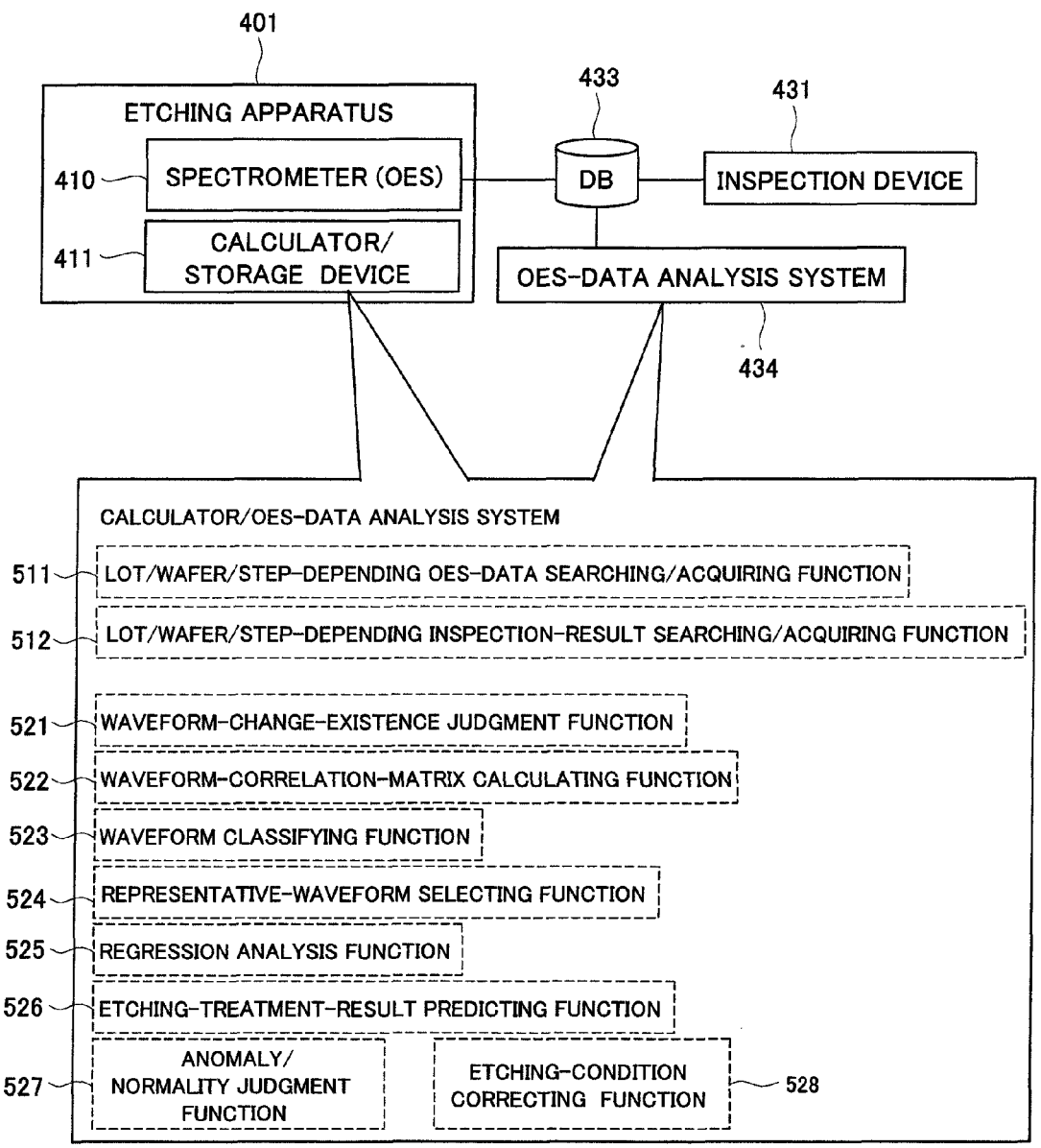
FIG. 5 is a schematic diagram showing a system configuration of etching treatment control of the etching apparatus according to the embodiment of the present invention.

Next, with reference to FIGS. 4 and 5, a configuration and an operation of the etching apparatus according to the embodiment of the present invention will be explained. FIG. 4 is a schematic diagram showing the configuration of the etching apparatus according to the embodiment of the present invention, and FIG. 5 is a schematic diagram showing a system configuration of etching treatment control of the etching apparatus according to the embodiment of the present invention.

In FIG. 4, the etching apparatus 401 includes: a chamber 402; an electrode 403; a wafer 405; an electrode 406; an exhaust system 407; a gas supply system 408; an apparatus controller/external communication device 409; a spectrometry (OES) 410; a calculator/storage device 411 which is a calculator system; and a screen/user interface 412 which is a terminal. A window 421 is provided on the chamber 402 so as to enter light 422 generated by the plasma into the spectrometer (OES) 410.

Also, the etching apparatus 401 is connected to an inspection device 431, a database (DB) 433, and an OES-data analysis system 434 serving as a calculator system via a network 432.

The chamber 402 is mounted in the etching apparatus 401, and the etching is performed inside the chamber 402. The wafer 405 is arranged so as to be sandwiched by the electrodes 403 and 406, and a surface of the wafer 405 is etched by generating the plasma 404 between the electrodes 403 and 406.

Note that the generation of the plasma 404 does not necessarily depend on the electrodes. A gas material required for the etching is introduced from the gas supply system 408, and a gas obtained after the etching reactions is exhausted from the exhaust system 407.

The plasma 404 causes optical emission, and the optical emission intensity of this light is detected by the spectrometer (OES) 410 in each wavelength of the light 422. The light inside the chamber 402 is introduced through the window 421. The spectrometer (OES) 410 and the apparatus controller/external communication device 409 are connected to the calculator/storage device 411 mounted in the etching apparatus 401, and the etching treatment is monitored by calculating and processing the spectra and the waveform by the calculator/storage device 411.

A plurality of OES data can be stored in the calculator/storage device 411. In accordance with a result of the monitoring, the anomaly/normality of the etching is judged, and besides, the etching treatment condition is corrected. The calculator/storage device 411 is connected to the screen/user interface 412, and a user performs the setting required for the calculation processing and confirms a result of the calculation processing via the screen/user interface 412.

Note that the spectrometer (OES) 410, the calculator/storage device 411, the screen/user interface 412 may be configured as independent analysis apparatuses to observe the optical emission of the plasma.

The spectrometer (OES) 410 and the apparatus controller/external communication device 409 are connected to the database (DB) 433 via the network 432, and the OES data or data of the etching treatment condition or a treatment work history can be stored in the database 433.

Also, the inspection device 431 for measuring the etching treatment result such as a line width obtained before/after the etching, CD (critical dimension: minimum gate dimension inside an LSI chip), and a film thickness is also similarly connected to the network 432, and an inspection result is stored in the database 433. The OES data, the data related to the etching treatment, and the inspection result stored in the database 433 are analyzed/evaluated by the OES-data analysis system 434.

Further, by acquiring the inspection result stored in the database 433 in the etching apparatus 401 by the apparatus controller/external communication device 409 of the etching apparatus 401, the etching condition can be corrected in the calculator/storage device 411 so as to reflect the inspection result.

Still further, the system configuration of the etching treatment control is as shown in FIG. 5, and various anomaly judgment processes are executed by functions 511 to 528 shown in FIG. 5.

Still further, the calculator/storage device 411 mounted in the etching apparatus 401 and the OES-data analysis system 434 commonly have each of functions 511 to 528.

Still further, each process performed by the functions 511 to 528 may be a process performed by only the calculator/storage device 411 or a process performed by only the OES-data analysis system 434.

In the etching apparatus 401, in order to classify the waveforms of the OES data and judge the anomaly/normality of the etching, first, the waveforms targeted for the classification are acquired by a lot/wafer/step-depending OES-data searching/acquiring function 511 which is optical-emission-intensity waveform acquiring means, no-changing waveforms are eliminated by a waveform-change-existence judgment function 521 which is waveform-change-existence judgment means, the correlation matrix is obtained by a waveform-correlation-matrix calculating function 522 which is waveform-correlation-matrix calculating means, and the waveforms are classified by a waveform classifying function 523 which is waveform classifying means.

A waveform is specified by a representative-waveform selecting function 524 which is representative-waveform selecting means, a wavelength at which the waveform is obtained is set as the monitored wavelength to perform the etching treatment, and the optical emission intensity at the wavelength is monitored. By a magnitude of the optical emission intensity, the anomaly/normality is determined by an anomaly/normality determining function 527.

Note that the lot means a treatment unit in which a plurality of wafers are collectively and continuously etched. The step means a treatment unit under one certain condition when one wafer is continuously treated under a plurality of conditions in the same chamber.

Also, in order to determine the anomaly/normality of the etching so as to correspond to the etching treatment result, first, the waveforms targeted for the classification are acquired by the lot/wafer/step-depending OES-data searching/acquiring function 511, the no-changing waveforms are eliminated by the waveform-change-existence judgment function 521, the correlation matrix is obtained by the waveform-correlation-matrix calculating function 522, the waveforms are classified by the waveform classifying function 523, and the waveform is selected by the representative-waveform selecting function 524.

Further, the etching treatment result measured by the inspection device 431 has been stored in the database 433, and the etching treatment result corresponding to the lot/wafer/step of the previously-classified waveform is acquired by a lot/wafer/step-depending inspection-result searching/acquiring function 512.

The pass/failure of the etching treatment result and the optical emission intensity at the wavelength of the selected waveform are corresponded to each other, or a relation between the etching treatment result and the optical emission intensity is analyzed/evaluated by a regression analysis function 525.

An anomaly/normality judgment criterion is determined, and the anomaly/normality is judged by the anomaly/normality judgment function 527 based on the optical emission intensity at the wavelength selected in the etching treatment. An error between a target etching treatment result and an actual etching treatment result is evaluated, and the etching treatment condition in the execution of the etching treatment is corrected by an etching-condition correcting function 528 with referencing the optical emission intensity at the monitored wavelength, so that the etching treatment result can be controlled.

In order to monitor an etching treatment with using a correlation coefficient of a waveform at one wavelength in a plurality of etching treatments, the target waveform is acquired by the lot/wafer/step-depending OES-data searching/acquiring function 511, and a correlation coefficient with the other waveform is obtained by the waveform-correlation-matrix calculating function 522 as taking a certain waveform obtained by performing the etching treatment once as a reference.

Also, the etching treatment result corresponding to the waveform to be targeted is acquired by the lot/wafer/step-depending inspection-result searching/acquiring function 512 to correspond the pass/failure of the etching treatment result to the obtained correlation coefficient, or the relation between the etching treatment result and the correlation coefficient is obtained by the regression analysis function 525 to determine the judgment criterion of the anomaly/normality, so that the anomaly/normality is judged by the anomaly/normality judgment function 527 with using the optical emission intensity at the wavelength selected in the etching treatment.

The error between the target etching treatment result and the actual etching treatment result is evaluated, and the etching treatment condition in the execution of the etching treatment is corrected by the etching-condition correcting function 528 with referencing the correlation coefficient of the waveform at the monitored wavelength, so that the etching treatment result can be controlled.

Further, based on the relation between the etching treatment result and the correlation coefficient obtained by the regression analysis function 525, the etching treatment result can be estimated by an etching-treatment-result predicting function 526 with using the correlation coefficient between the waveform obtained in the etching treatment and the reference waveform.

Figure 6:
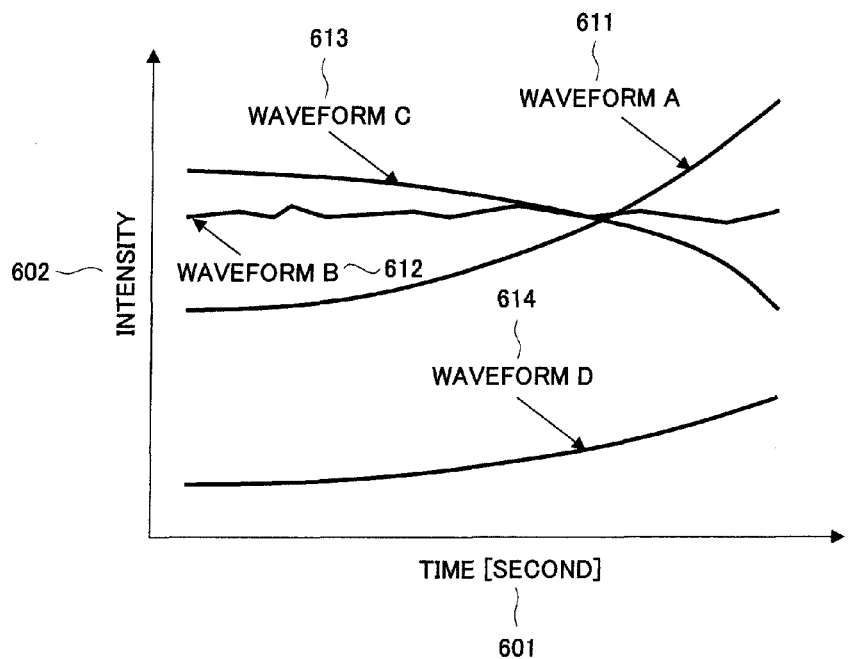
FIG. 6 is an explanatory diagram for explaining a correlation between waveforms in the etching apparatus according to the embodiment of the present invention.
Figure 7:
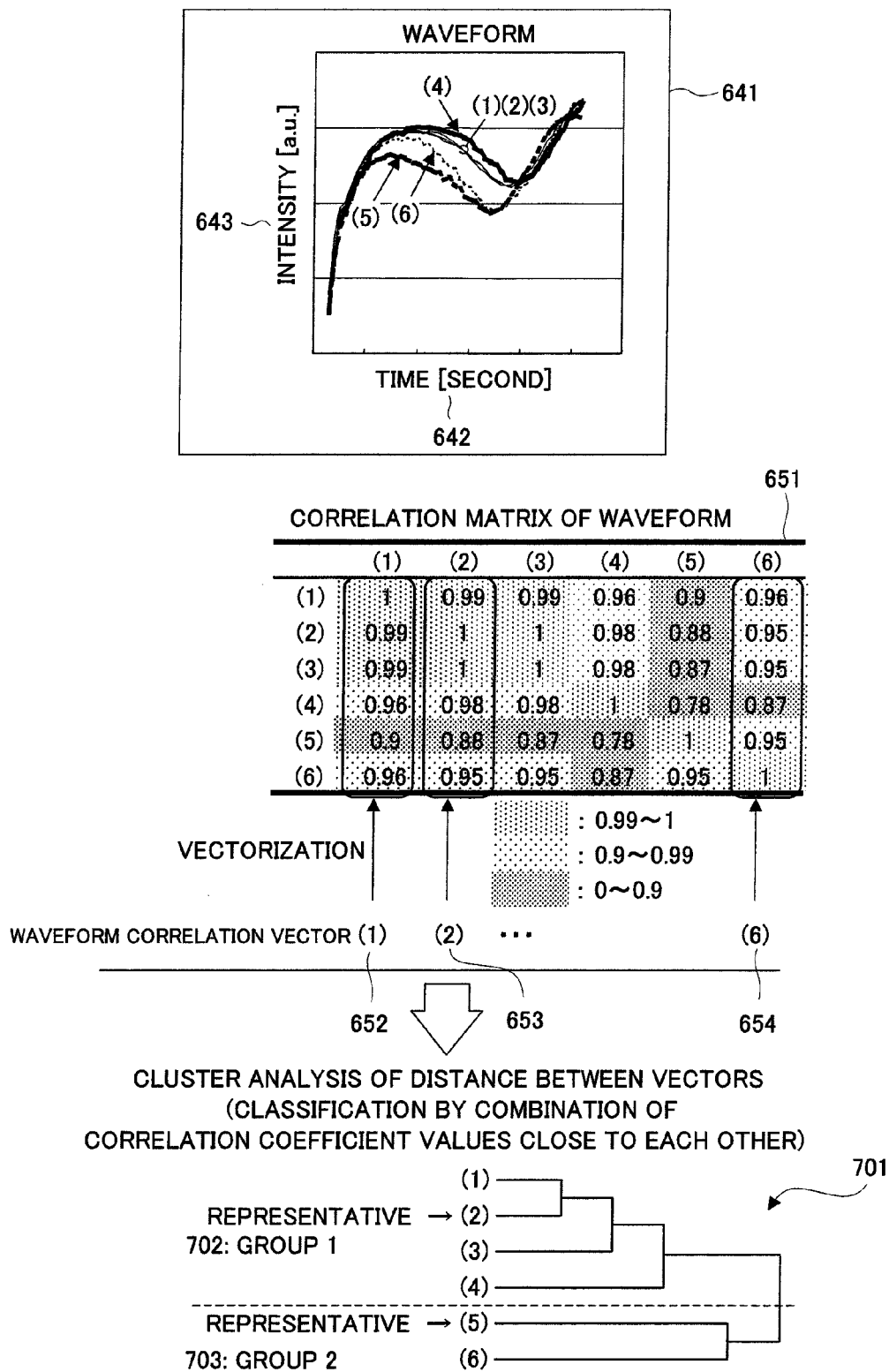
FIG. 7 is an explanatory diagram for explaining an outline of cluster analysis in the etching apparatus according to the embodiment of the present invention.
Figure 9:
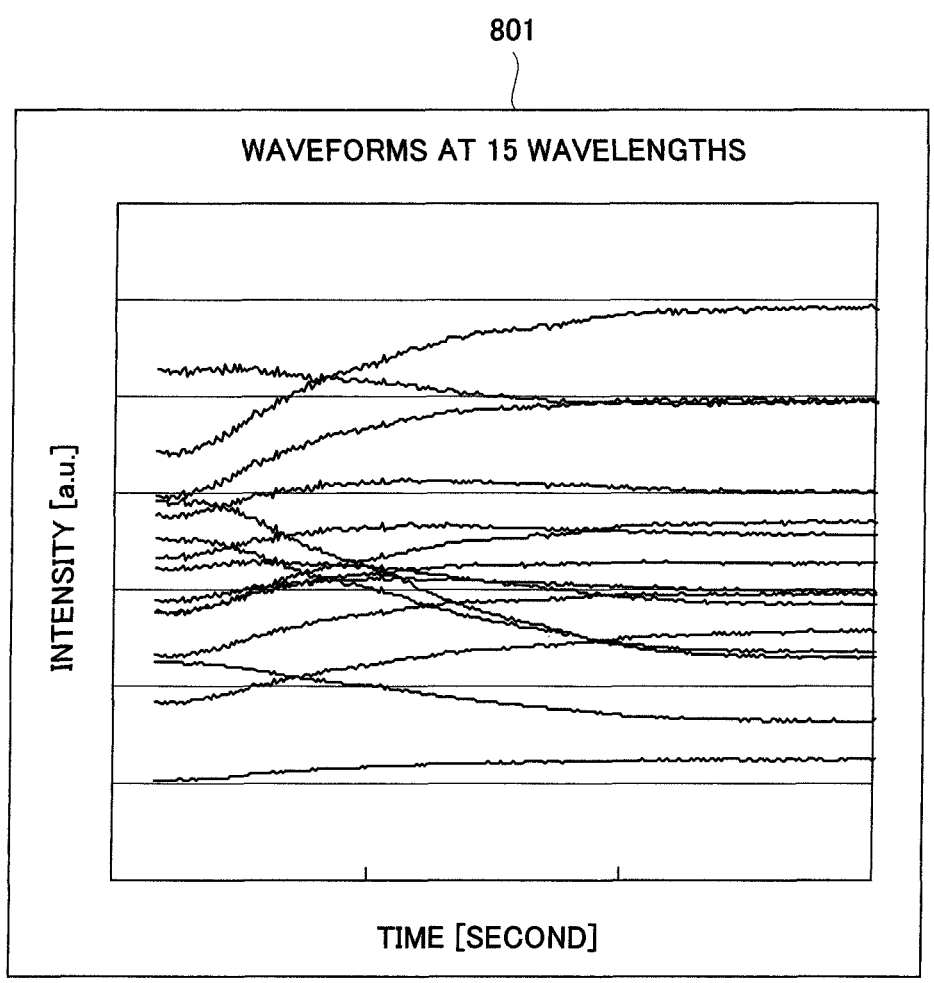
FIG. 9 is a diagram showing an example of waveforms at 15 wavelengths in the etching apparatus according to the embodiment of the present invention.
Figure 11:
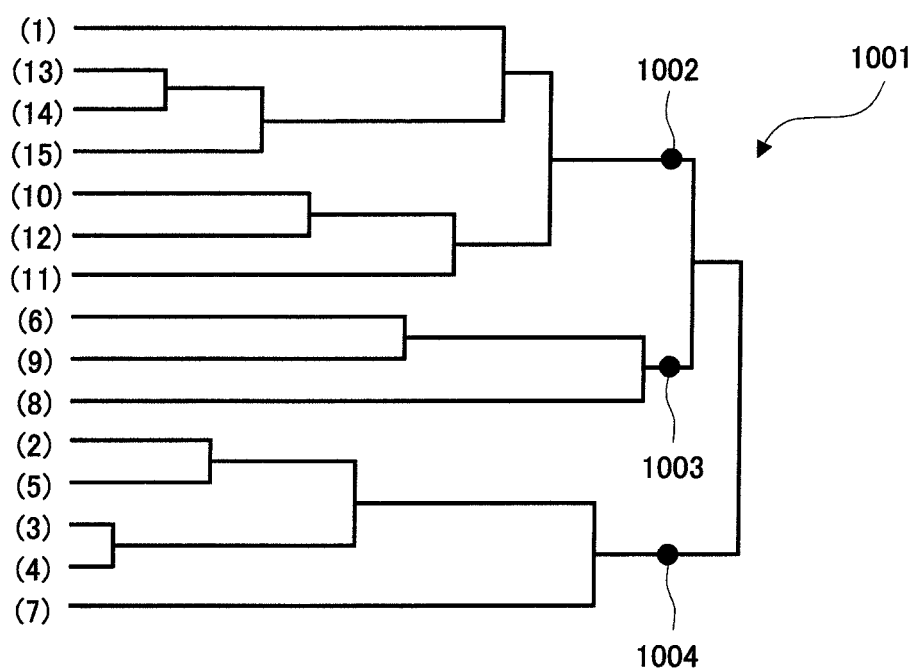
FIG. 11 is a diagram showing an example of a result of the cluster analysis based on a correlation matrix of waveforms at 15 wavelengths in the etching apparatus according to the embodiment of the present invention.
Figure 13:
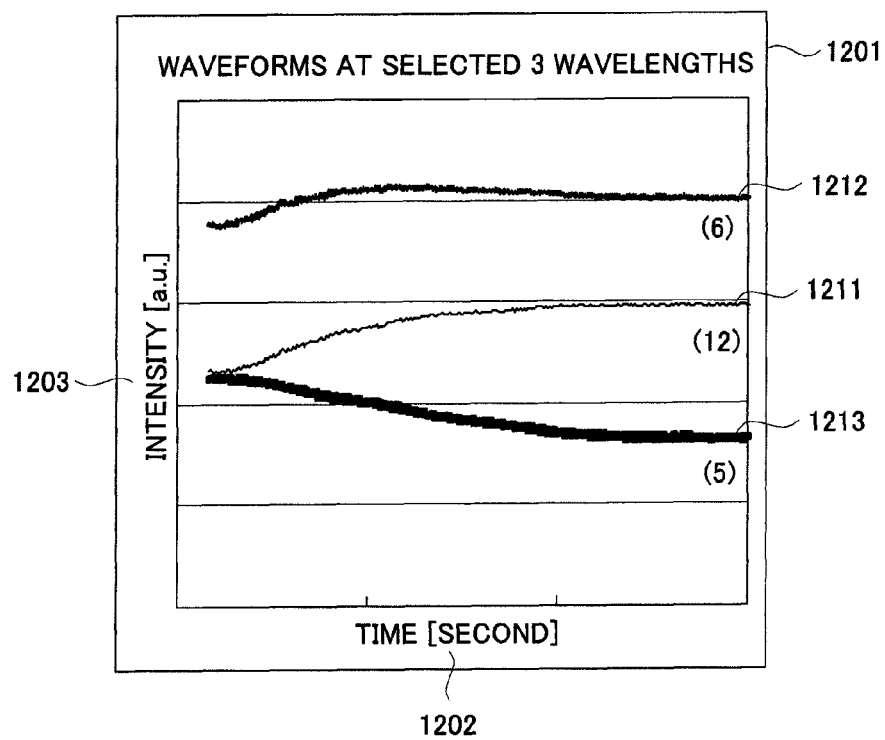
FIG. 13 is a diagram showing waveforms at selected three wavelengths in the etching apparatus according to the embodiment of the present invention.

Next, with reference to FIGS. 6 to 13, a method of classifying the waveforms at the plurality of wavelengths in the etching apparatus according to the embodiment of the present invention to obtain the wavelength from the representative waveform will be described. FIG. 6 is an explanatory diagram for explaining a correlation between waveforms in the etching apparatus according to the embodiment of the present invention, FIG. 7 is an explanatory diagram for explaining an outline of cluster analysis in the etching apparatus according to the embodiment of the present invention, FIG. 8 is an explanatory diagram for explaining an outline of a calculation method of the cluster analysis in the etching apparatus according to the embodiment of the present invention, FIG. 9 is a diagram showing an example of waveforms at 15 wavelengths in the etching apparatus according to the embodiment of the present invention, FIG. 10 is a diagram showing an example of a correlation matrix of the 15 wavelengths in the etching apparatus according to the embodiment of the present invention, FIG. 11 is a diagram showing an example of a result of the cluster analysis based on the correlation matrix of the waveforms at the 15 wavelengths in the etching apparatus according to the embodiment of the present invention, FIG. 12 is a diagram showing an example of a group-depending correlation matrix of the waveforms at the 15 wavelengths in the etching apparatus according to the embodiment of the present invention, and FIG. 13 is a diagram showing waveforms at selected three wavelengths in the etching apparatus according to the embodiment of the present invention.

For the waveforms at the plurality of wavelengths in the OES data in the plurality of etching treatments, a method of classifying the waveforms with using the correlation matrix between the waveforms and selecting the representative waveform is called waveform correlation cluster analysis.

The classification of the waveforms is to collect the waveforms having similar "shapes" as the same group, that is, a cluster. The waveform is a "curve" expressing intensity along the time axis, and therefore, a similarity of the shapes can be evaluated by a correlation coefficient.

FIG. 6 shows a graph of four waveforms. In FIG. 6, the four waveforms are shown as taking time [second] 601 on an "x" axis and optical emission intensity 602 on a y axis.

When intensity is focused, a waveform A611, a waveform B612, and a waveform C613 are close to each other. However, if the classification is based on covariant characteristics of the chemical reaction, the waveform A611 and a waveform D614 having similar shapes with each other are supposed to be in a common group.

According to the correlation coefficient, with respect to the waveform A611, the waveform B612 is "−1", the waveform C613 is "0", and the waveform D614 is "1". That is, if the correlation coefficient is close to "1", the waveforms are similar to each other. Contrarily, if it is away from "1", the waveforms are not similar to each other.

A correlation of the other waveform with respect to the waveform A611 can be expressed as a vector 621. Also with respect to the waveform B612, the waveform C613, and the waveform D614, the correlations thereof can be similarly expressed as a vector 622, a vector 623, and a vector 624. When the vector 621 and the vector 624 of the waveform A611 and the waveform D614 are compared with each other, the vectors match each other.

On the other hand, in the vector 622 and the vector 623 of the waveform B612 and the waveform C613, there are no close values to each other. Accordingly, by using these vectors, the similarities of the various waveforms can be quantified, so that the waveforms can be numerically classified. These vectors are called waveform correlation vectors.

The waveform correlation vector is obtained by arranging the correlation coefficient with each waveform, and therefore, can be obtained by calculating a correlation matrix such as a matrix 631 shown in FIG. 6.

The correlation matrix "R" is calculated by the following equations (1) to (4) with using the optical emission intensity data (the number of pieces of data "n" and the number of waveforms "m") $x_{ij}$ at each sampling time point.

[Formula 1]

$$R = [\rho_{kl}] \quad (1)$$

$$\rho_{kl} = \frac{\text{cov}(x_k, x_l)}{\sqrt{\text{var}(x_k) \cdot \text{var}(x_l)}} \quad (2)$$

$$\text{cov}(x_k, x_l) = \frac{1}{n}\sum_{i=0}^{n-1}(x_{ik} - \bar{x}_k)(x_{il} - \bar{x}_l) = \frac{1}{n}\sum_{i=0}^{n-1}x_{ik}x_{il} - \bar{x}_k\bar{x}_l \quad (3)$$

$$\text{var}(x_k) = \frac{1}{n}\sum_{i=0}^{n-1}(x_{ik} - \bar{x}_k)^2 = \frac{1}{n}\sum_{i=0}^{n-1}x_{ik}^2 - \bar{x}_k^2 \quad (4)$$

Here, symbols "k" and "l" are indexes corresponding to the waveforms, which take numbers of 0 to (m−1), and the correlation matrix R is a matrix of "m×m". A bar "−" above a variable means an average.

FIG. 7 shows an outline of the waveform correlation cluster analysis in which six waveforms are exemplified.

In a waveform graph 641, the six waveforms (1) to (6) are shown as taking time [second] 642 on an x axis and optical emission intensity 643 on a y axis. Each waveform expresses the optical emission intensity with respect to the etching treatment time at optical emission wavelengths such as wavelengths of 515 [nm], or 803 [nm].

The waveforms (1), (2), and (3) are overlapped with each other in an entire time region and have a similar waveform. The waveform (4) (thick solid line) has slightly higher optical emission intensity than those of the waveforms (1), (2), and (3).

On the other hand, the waveform (5) (thick dotted line) and the waveform (6) (dotted line) have low optical emission intensities. A correlation matrix 651 between these waveforms is calculated, and each row or each column of the correlation matrix 651 between the waveforms is set as a waveform correlation vector ((1) 652, (2) 653, to (6) 654) of one waveform with respect to the other waveform.

In FIG. 7, each column is vectorized. In the waveform correlation vectors of the waveforms (1), (2), and (3), each component value is very close to the other. In the waveform correlation vector of the waveform (4), while values of the correlation coefficients with respect to the waveforms (5) and (6) are small, values of the correlation coefficients with respect to the waveforms (1), (2), and (3) are large, that is close to the waveform correlation vectors in the waveforms (1), (2), and (3). On the other hand, in the waveforms (5) and (6), their values are away from those of the waveform correlation vectors in the waveforms (1) to (4). Accordingly, by performing the cluster analysis for these waveform correlation vectors, the waveforms can be classified (for example, by a cluster analysis result (dendrogram) 701 of FIG. 7, the waveforms can be classified into a group 1 (702) and a group 2 (703)).

The cluster analysis is a method in which, first, two clusters whose distance therebetween is the shortest as taking a point position on a coordinate space as a target are integrated (clustered) to form a new cluster. In the method, after the clustering, the shortest distance is further searched, and the clustering is repeated until one cluster is finally formed. The data can be classified in accordance with some clusters during the clustering. The waveform correlation vector can be expressed as a position in a multivariate coordinate space, and therefore, the waveforms can be classified by the cluster analysis.

The outline of the cluster analysis is shown in FIG. 8.

As an example of the classification shown in FIG. 8, a position on a two-dimensional space is shown. First, in distance evaluation 1 (710), all distances between positions (1) to (5) are obtained to obtain the shortest position combination (2) and (3). In integration 1 (720), the positions (2) and (3) are clustered as a cluster 721, and a position 722 representing the two positions is determined by a gravity-center position.

Subsequently, in distance evaluation 2 (730), distances between a cluster 731 and the positions (1), (4), and (5) which are not in the cluster are obtained to obtain a combination of the shortest position between (1) and the cluster 731. In integration 2 (740), the position (1) is clustered to obtain a cluster 741, and the representative position is changed from the position 742 to a position 743.

In distance evaluation 3 (750), distances between a cluster 751 and the positions (4) and (5) are obtained to obtain a combination of the shortest position between (4) and (5).

And, in integration 3 (760), the positions (4) and (5) are newly clustered as a cluster 761, and a representative position 762 is obtained. In this manner, finally, the one cluster is obtained. If they are to be classified into two, the classification is determined by the cluster 751 and the cluster 761.

As a method of classifying the data by forming the clusters, a "k-means" method and a self-organization map can be also used.

The k-means method is a method of obtaining the clusters by previously determining the number of division and obtaining a combination of a representative position at which a sum of distances from data positions is minimized and the data close to the representative position. This algorithm is described as follows.

1. A data set is randomly divided into the specified number of division to form initial clusters.
2. The gravity-center position of the data contained in each cluster is calculated.
3. For all data, the data is allocated to a cluster which is the closest to the gravity-center position of each cluster calculated in the step of 2.
4. If the data contained in the cluster is not different from that at a previous repetition, the clustering is finished. Otherwise, the step returns to the step of 2, and the procedure is repeated again.

The self-organization map is a method, for high-dimensional vector data, of arranging the data closer to each other on a two-dimensional map as the data whose difference (distance therebetween) is closer. A vector value is set at each position of the two-dimensional map, the vector value at each position on the map is corrected from a value of each data by the repetitive calculation, and each data is arranged on the map. As a result, the data is two-dimensionally arranged, and therefore, the data is classified based on this arrangement. The method has an advantage that a classification result or a position relation between the clusters can be easily confirmed.

After dividing the waveforms by referencing the waveform correlation vector, the representative waveform is obtained.

The method of the classification based on the waveform correlation vector to obtain the representative waveform is explained by using waveforms at 15 wavelengths shown in FIG. 9 as an example.

The waveforms shown in FIG. 9 express change of the optical emission intensity with respect to the time [second]. As the waveform targeted for the classification, a waveform at a wavelength which peaks in a spectrum highly related to a substance is referenced. For example, as shown in the optical-emission spectrum distribution 111 of FIG. 1, there are a lot of wavelengths which peak in the spectrum, and therefore, there are a lot of waveforms targeted for the waveform classification.

A correlation matrix obtained by calculating the waveforms at the 15 wavelengths shown in FIG. 9 based on the above-described equations (1) to (4) is shown in FIG. 10.

Any of rows and columns of the matrix correspond to each waveform, and are denoted by numbers (1) to (15). In FIG. 9, as seen from the figure such that some waveforms tend to upward and the other waveforms tend to downward, the waveforms having the same tendency have a positive correlation coefficient therebetween. In a case of the waveforms which are particularly similar to each other, the correlation coefficient therebetween is close to 1.

On the other hand, the correlation coefficient between the waveforms having the opposite tendency to each other (one waveform is upward and the other waveform is downward) is negative.

By setting each row or each column of the correlation matrix as the vector, the waveform correlation vector for each waveform can be obtained. A result of the cluster analysis for the waveform correlation vector is shown as a dendrogram 1001 of FIG. 11.

In a case of three-type classification, at three branch positions 1002, 1003, and 1004 of the dendrogram 1001, waveforms existing in a left side from the positions in FIG. 11 are classified as respective groups.

In order to determine the number of classification, values may be referred, the values being such as the distance between the clusters, an average of the waveform correlation vectors contained in the clusters, the minimum value of the correlation coefficients in the waveform correlation vectors contained in the clusters, or the maximum value thereof.

FIG. 12 shows a correlation matrix between the waveforms which belong to each group as the result of the three-type classification.

Because of the correlation matrix between the similar waveforms, the correlation coefficient therebetween is close to 1. In order to obtain the representative waveform, if the criterion is set so that a similar waveform with a particularly high correlation coefficient in the group is the representative, a waveform whose correlation coefficient average is maximized among the waveforms in the group may be the representative waveform.

A waveform (12) 1121 is the representative in a group 1, a waveform (6) 1122 is the representative in a group 2, and a waveform (5) 1123 is the representative in a group 3.

The waveforms 1201 at the selected three wavelengths are shown in FIG. 13. The group 1 is classified as the upward tendency which is similar to that of the waveform (12) 1211, the group 2 is classified as the upward and downward tendency in the waveform (6) 1212, and the group 3 is classified as the downward tendency in the waveform (5) 1213. The wavelengths at these waveforms can be the wavelengths to be monitored.

If the reference is set so that any waveform in the group is the representative as an average waveform, a waveform having a combination of a correlation coefficient which is the closest to the average of the correlation coefficients of the waveforms in each group may be the representative. In order to obtain a shape of the representative waveform, an average of the waveforms themselves in the same group may be used for reducing variations.

By obtaining the wavelength to be monitored in this manner, the waveform, that is, the optical emission intensity, at the specific wavelength from the OES data can be monitored in a subsequent actual etching treatment. By setting the judgment criterion of the anomaly or normality, the etching apparatus or the etching treatment can be monitored with the anomaly/normality judgment.

The relation between the plurality of etching treatment results obtained by the inspection and the waveform, that is the optical emission intensity, at the selected wavelength can be analyzed/evaluated, and besides, the etching performance can be evaluated in the actual etching treatment and the etching treatment result can be estimated by modeling the relations between the waveform, the optical emission intensity, and the etching treatment results, for example with using the mathematical equation or others.

Further, by modeling the relation with the etching treatment condition, an etching condition in the subsequent etching treatment can be corrected by monitoring the waveform or the optical emission intensity at the specific wavelength in the etching treatment and inspecting the etching treatment result as needed.

Figure 14:
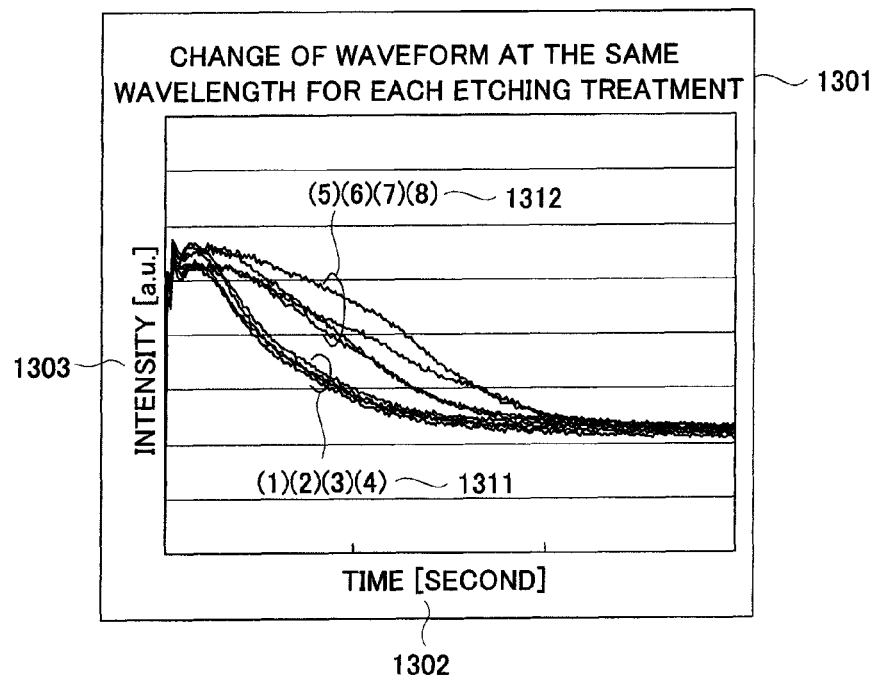
FIG. 14 is a diagram showing an example of waveforms obtained by performing the etching treatment 8 times at the same wavelength in the etching apparatus according to the embodiment of the present invention.
Figure 16:
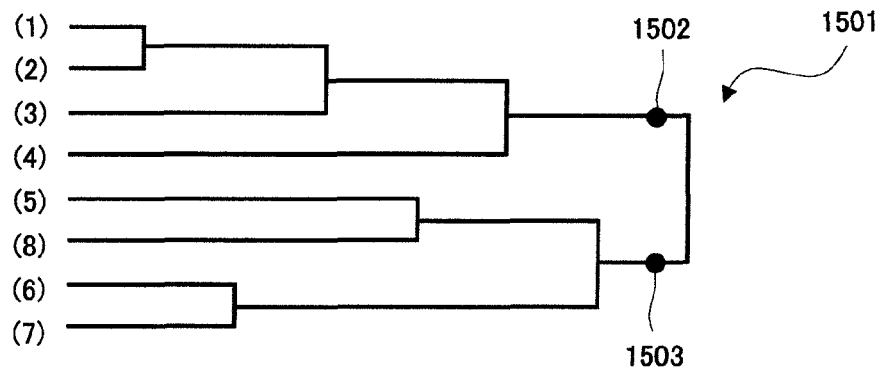
FIG. 16 is a diagram showing an example of a result of the cluster analysis based on the correlation matrix between 8 waveforms at the same wavelength in the etching apparatus according to the embodiment of the present invention.
Figure 17:
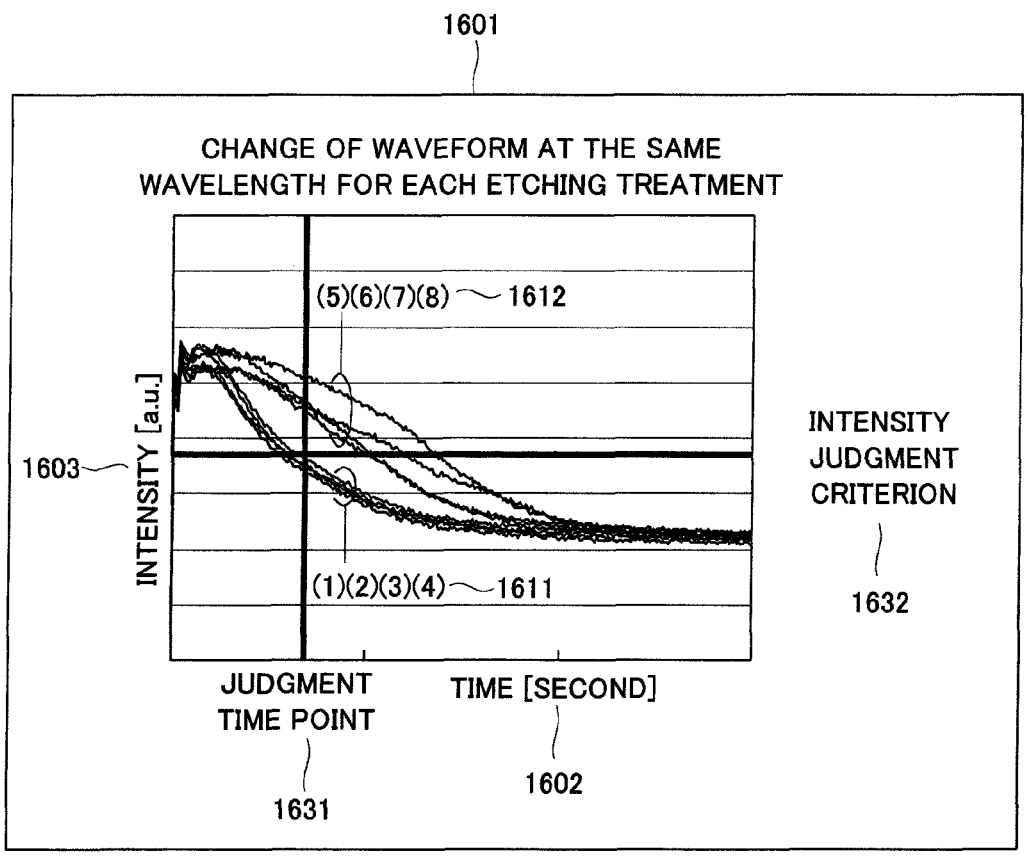
FIG. 17 is a diagram showing an example of an intensity judgment criterion of the waveforms at the same wavelength in the etching apparatus according to the embodiment of the present invention.

Next, with reference to FIGS. 14 to 17, a method for monitoring and analyzing/evaluating a difference in the waveform for each etching treatment at a certain specific wavelength in the etching apparatus according to the embodiment of the present invention will be explained. FIG. 14 is a diagram showing an example of waveforms obtained by performing the etching treatment 8 times at the same wavelength in the etching apparatus according to the embodiment of the present invention, FIG. 15 is a diagram showing an example of a correlation matrix between 8 waveforms at the same wavelength in the etching apparatus according to the embodiment of the present invention, FIG. 16 is a diagram showing an example of a result of the cluster analysis based on the correlation matrix between the 8 waveforms at the same wavelength in the etching apparatus according to the embodiment of the present invention, and FIG. 17 is a diagram showing an example of an intensity judgment criterion of the waveforms at the same wavelength in the etching apparatus according to the embodiment of the present invention.

In performing the etching treatment 8 times, FIG. 14 shows change 1301 of a waveform at the same wavelength for each etching treatment.

These waveforms are obtained when films of the same-type LSI products are etched, and their recipes (etching treatment conditions) are also the same. An execution order of the etching treatments are sequentially from (1), (2), (3), to (8). Compared to [(1), (2), (3) and (4)] which are the earlier treatments, in the later treatments [(5), (6), (7) and (8)] 1312, the decrease in the optical emission intensity is slowed down on the time [second] 1302 to provide a largely-different waveform. Accordingly, based on the difference, the waveforms are classified by the waveform correlation cluster analysis.

FIG. 15 shows a correlation matrix between the waveforms (1) to (8).

The values of the correlation coefficients between the waveforms (1) to (4) are large, and the values of the correlation coefficients between the waveforms (5) to (8) are also large. By setting each row or each column of the correlation matrix as the waveform correlation vector, the cluster analysis is performed.

A resultant dendrogram 1501 is shown in FIG. 16.

Based on the distance between the clusters, the waveforms can be classified into a cluster of (1), (2), (3), and (4) and a cluster of (5), (6), (7), and (8) at branching positions 1502 and 1503. In this manner, by classifying the waveforms at the same wavelength in the series of etching treatments, it can be automatically determined by the calculator process that the change of the etching treatment has been caused after performing the etching treatment up to (1), (2), (3), and (4).

In response to this change, for example, an etching rate is increased, and a gate dimension is narrowed. This means that, since the decrease in the optical emission is slowed down, the etching rate is increased. Therefore, if the optical emission intensity is high, it can be determined that the anomaly has been caused.

As shown in the change 1601 of the waveforms at the same wavelength for each etching treatment in FIG. 17, by setting a criterion 1632 for judging the intensity and a time point 1631 at which the slow down of the decrease in the optical emission intensity is determined, the anomaly of the etching treatment can be judged at a time point when the waveforms are acquired in the etching treatment.

Figure 18:
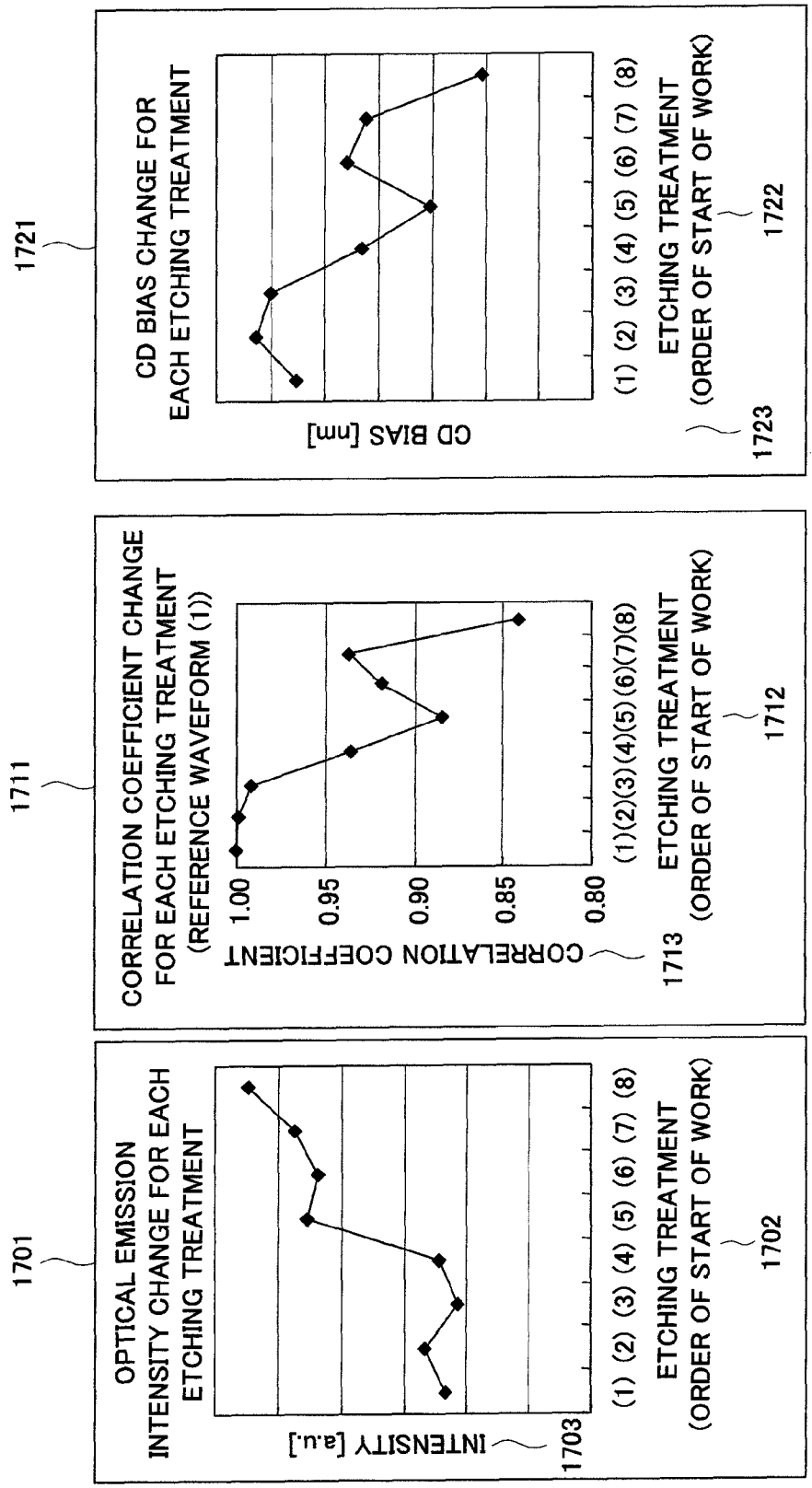
FIG. 18 is a diagram showing an example of changes in an optical emission intensity, a correlation coefficient between waveforms, and a CD bias for each etching treatment in the etching apparatus according to the embodiment of the present invention.

Next, with reference to FIG. 18, a method of quantifying the difference among the waveforms at a certain specific wavelength for each etching treatment in the etching apparatus according to the embodiment of the present invention with using the correlation coefficient to monitor the etching treatment will be explained. FIG. 18 is a diagram showing an example of changes in the optical emission intensity, the correlation coefficient between the waveforms, and a CD bias for each etching treatment in the etching apparatus according to the embodiment of the present invention.

Here, the eight waveforms shown in the above-described FIG. 14 are exemplified and explained with reference to also the above-described FIGS. 15 to 17.

First, by using one certain waveform as the reference, the correlation coefficient with the other waveform is obtained. This step corresponds to the calculation of the correlation coefficient with fixing the index k in the above-described equations (1) to (4). For example, if the waveform (1) is used as the reference, the changes of the correlation coefficients in the etching from (1) to (8) are shown in a first column (1, 0.999, 0.992, 0.936, 0.885, 0.919, 0.938, and 0.841) of the correlation matrix shown in FIG. 15.

In performing the etching treatment 8 times, FIG. 18 shows the changes of the optical emission intensity, the correlation coefficient in the case of using the waveform (1) as the criterion, and the CD bias.

A symbol "CD" (Critical Dimension) is a gate dimension, and particularly indicates a gate whose width is narrow in an LSI chip. The CD bias is a difference between a gate dimension of the etching treatment result and a width of a resist formed on the gate in etching the gate.

As the optical emission intensity change 1701 for each etching treatment, the optical emission intensity at a judgment time point 1631 in FIG. 17 is plotted for each etching treatment.

There is a clear intensity difference between intensities shown by (1), (2), (3), and (4) and intensities shown by (5), (6), (7), and (8) in FIG. 17.

However, according to the CD bias change 1721 for each etching treatment, the CD bias has already been decreased in the etching treatment (4). According to the correlation coefficient change 1711 for each etching treatment, similarly to the CD bias change 1721, the decrease in the correlation coefficient value is observed in the etching treatment (4).

This is because not the information of the optical emission intensity at one certain time point but the change of the optical emission intensity, that is, waveform, during the etching treatment is effective for the etching treatment performance. Accordingly, by monitoring the etching treatment with using the correlation coefficient, the etching treatment can be judged with high accuracy.

Note that the waveforms in the entire etching treatment time are used for the calculation of the correlation coefficient here. However, the correlation coefficient may be calculated with using the waveforms obtained until a certain time point during the etching treatment or the waveforms obtained in a certain time range during the entire etching treatment.

In the monitoring with using the correlation coefficient, by quantifying the correspondence between the correlation coefficient value and the etching treatment result based on a mathematical equation, the etching treatment result can be estimated at a stage where the etching treatment is performed, and the etching treatment can be monitored or the anomaly/normality can be judged based on an estimated value.

In a case of modeling with using a first-order linear relation in which a correlation coefficient of a wavelength at one wavelength is taken as an input "x" and one etching treatment result is taken as an output "y", a mathematical equation is expressed as an equation (5).

[Formula 2]

$$y = ax + b \qquad (5)$$

Here, a symbol "a" represents a coefficient, and a symbol "b" represents an intercept. The coefficient and the intercept can be determined by multiple regression analysis with using actual values. For the determination whether the etching treatment is monitored with using the estimated value based on the mathematical equation shown as the equation (5) or not, if a correlation coefficient between the estimated value and the actual value of the output y by the model is high (close to 1), the determination may be made so that the monitoring can be achieved.

For the judgment of the anomaly/normality, a judgment criterion such as an upper limit and a lower limit maybe set. The number of terms of each of the input x and the output y may be multivariate. In a case that only the input x is multivariate, similarly to the determination of the coefficient and the intercept of the equation (5), the coefficient of the equation may be determined by multiple regression analysis.

In a case that both of the input x and the output y are multivariate, the coefficient may be determined by regression analysis called PLS (Partial Least Square) method.

Figure 20:
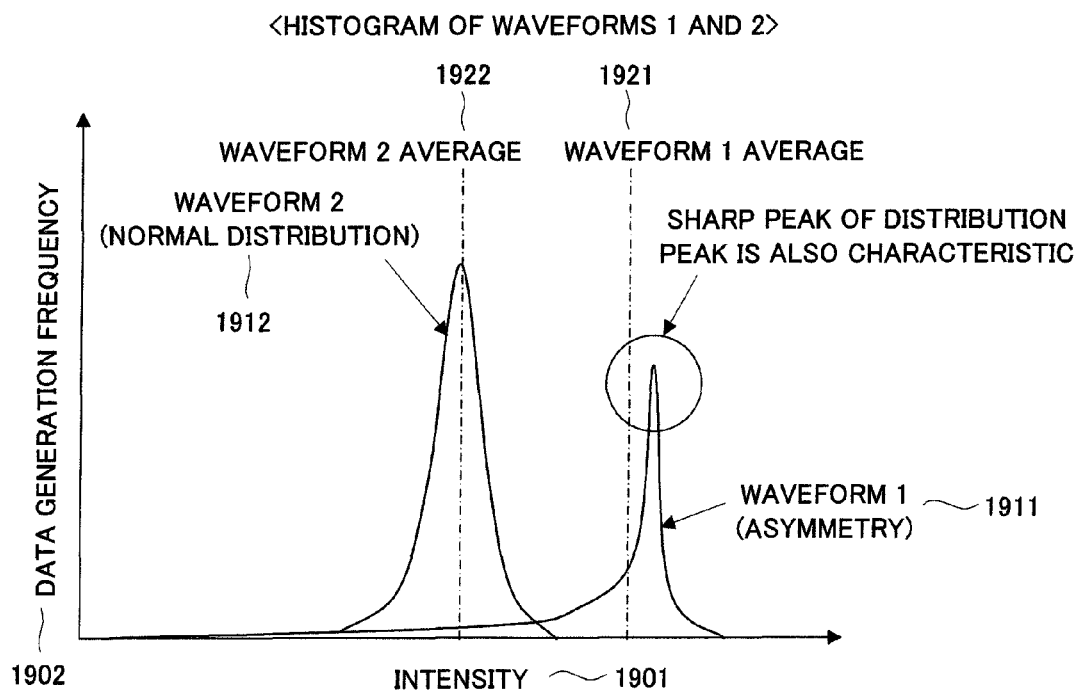
FIG. 20 is a diagram showing an example of a histogram with respect to an optical emission intensity of the waveform containing variation in the etching apparatus according to the embodiment of the present invention.
Figure 21:
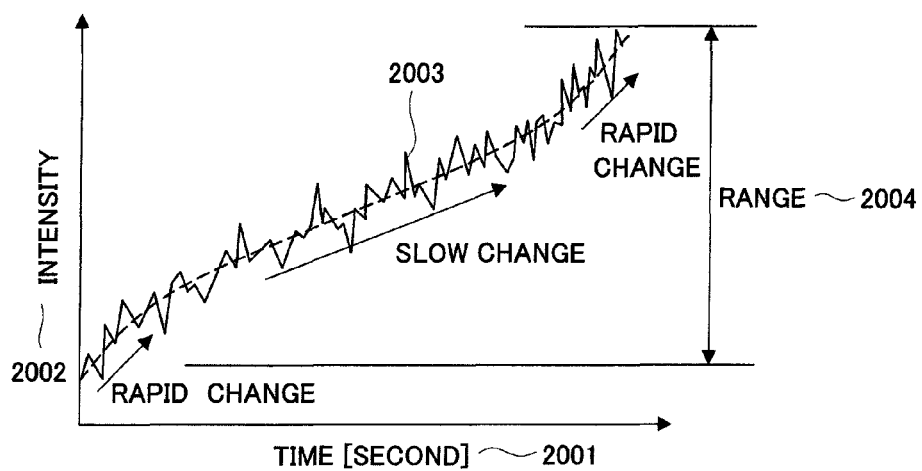
FIG. 21 is a diagram showing another example of the waveform containing variation in the etching apparatus according to the embodiment of the present invention.
Figure 22:
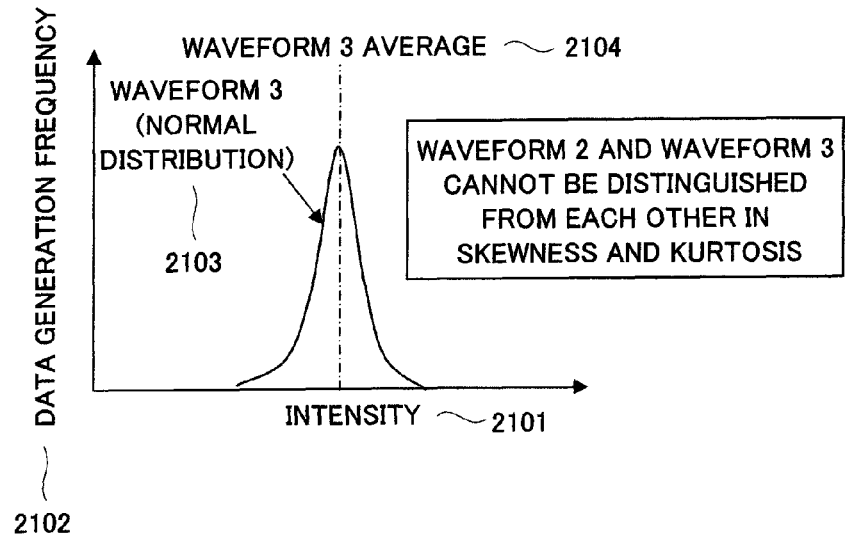
FIG. 22 is a diagram showing another example of a histogram with respect to an optical emission intensity of the waveform containing variation in the etching apparatus according to the embodiment of the present invention.
Figure 23:
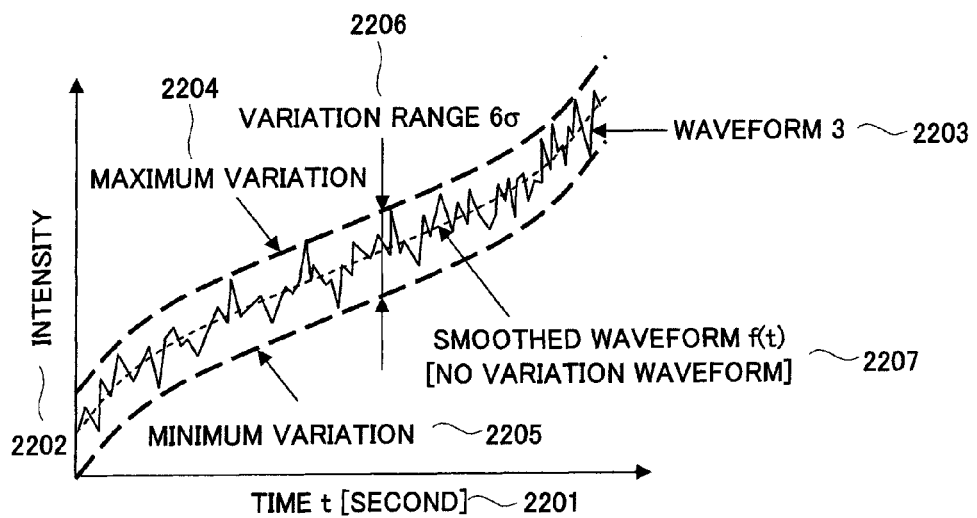
FIG. 23 is an explanatory diagram for explaining a variation range of the waveform containing variation in the etching apparatus according to the embodiment of the present invention.
Figure 24:
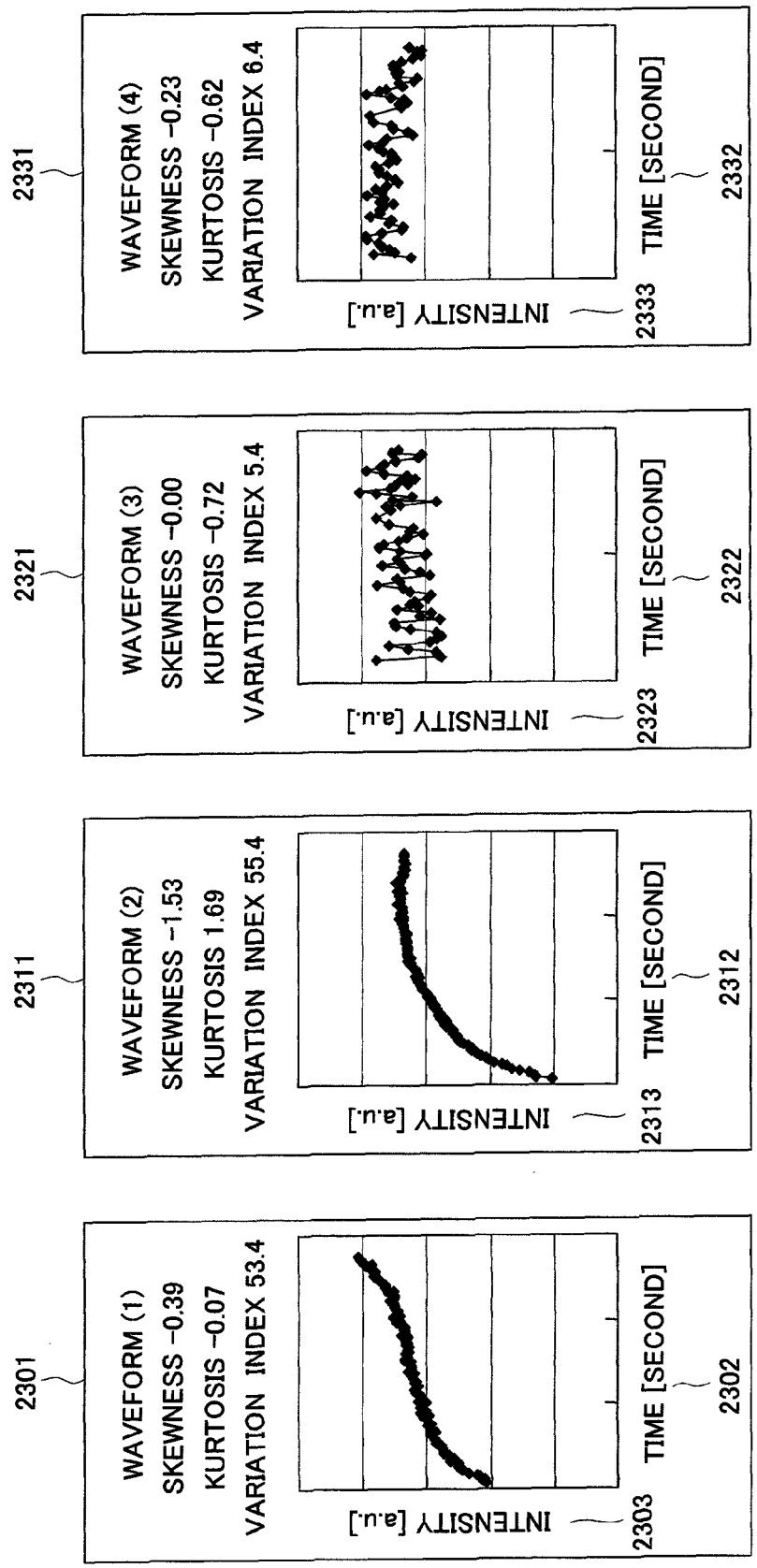
FIG. 24 is diagrams showing an example of the skewness, kurtosis, and variation index of the waveform containing variation in the etching apparatus according to the embodiment of the present invention.

Next, with reference to FIGS. 19 to 24, a method of judging the existence of the change of the waveform, that is, the optical emission intensity, with respect to the etching treatment time in the etching apparatus according the embodiment of the present invention will be explained. FIG. 19 is a diagram showing an example of a waveform containing variation in the etching apparatus according to the embodiment of the present invention, and shows waveforms with/without the intensity change. FIG. 20 is a diagram showing an example of a histogram of the waveform containing the variation with respect to the optical emission intensity in the etching apparatus according to the embodiment of the present invention, FIG. 21 is a diagram showing an example of the waveform containing the variation in the etching apparatus according to the embodiment of the present invention, FIG. 22 is a diagram showing an example of another histogram of the waveform containing the variation with respect to the optical emission intensity in the etching apparatus according to the embodiment of the present invention, FIG. 23 is an explanatory diagram for explaining a variation range of the waveform containing the variation in the etching apparatus according to the embodiment of the present invention, and FIG. 24 is a diagram showing an example of the skewness, kurtoses, and variation index of the waveform containing the variation in the etching apparatus according to the embodiment of the present invention.

First, in order to judge the existence of the waveform change, the change is quantified. Since the waveform data contains the variation, it is required to remove the influence of the variation for the evaluation with using a rate of change or a curvature. Further, since a change manner (a time point at which the change is caused or a magnitude of the change) is various depending on the waveform, it is required to previously analyze the waveform for determining a criterion time point/intensity in the change detection.

The judgment of the existence of the change with using the rate of change or curvature is largely restricted or limited in practical use. Accordingly, a method of summarizing the optical emission intensity data of the waveform containing the variation and quantifying with using its statistics is employed.

FIG. 19 shows a waveform 1 (1803) with the change and a waveform 2 (1813) containing the variation but without the change.

It is assumed that the variation is as white noise, that is, a frequency of generating the variation is as following a normal distribution. Therefore, a frequency of generating the intensity of the waveform 2 (1813) is as the normal distribution whose center has a certain constant intensity. In the waveform 1 (1803), the intensity is upward as containing the variation, and converges at a certain intensity.

FIG. 20 shows the histogram in which the generation frequencies of the intensities of these waveforms are compared with each other.

In FIG. 20, an "x" axis represents the intensity, and a "y" axis represents the generation frequency of the data at the intensity of the x axis. A distribution 1912 of the waveform 2 is a normal distribution whose center is at an intensity of an average 1922 of the waveform 2.

On the other hand, a distribution 1911 of the waveform 1 is an asymmetric distribution in which peaks of an average 1921 of the waveform 1 and a mode value of the distribution is shifted from each other. There is also a characteristic that the peaks are sharper than that of the normal distribution.

In order to quantify such a difference in the frequency distribution, the statistics such as skewness and kurtosis may be used.

A skewness "γ1" is defined by the following equation (6), and a kurtosis "γ2" is defined by the following equation (7). Note that the equations are based on a population from which a bias (constraint condition) in a sample is removed.

[Formula 3]

$$\gamma_1 = \frac{n}{(n-1)(n-2)} \sum_i^n \left(\frac{x_i - \bar{x}}{\sigma}\right)^3 \quad (6)$$

$$\gamma_2 = \frac{n(n+1)}{(n-1)(n-2)(n-3)} \sum_i^n \left(\frac{x_i - \bar{x}}{\sigma}\right)^4 - \frac{3(n-1)^2}{(n-2)(n-3)} \quad (7)$$

$$\sigma = \sqrt{\frac{\sum_i^n (x_i - \bar{x})^2}{n-1}} \quad (8)$$

Here, a symbol "x" represents a target data, that is, a sample of the optical emission intensity. A symbol "σ" represents a standard deviation which is defined by the above-described equation (8). A symbol "n" represents the number of pieces of data.

Here, the equations based on the population are shown. However, even when the skewness and kurtosis are calculated by equations based on the sample, the objective distribution bias can be quantified. If both of the skewness and kurtosis are 0 (zero), the distribution is a normal distribution. That is, if they are close to 0, the waveform contains only the variation, and has a constant intensity.

Contrarily, if they have a value away from 0 such as 1, the waveform changes with containing the variation. Note that, if the skewness has a positive value, a foot of the distribution is lengthened toward a right side, and, if the kurtosis is positive, it is a sharper distribution than the normal distribution.

However, if the waveform has a change expressed by a third-order function or a fifth-order function, the histogram may be the normal distribution in some cases.

FIG. 21 shows an example of such a waveform [waveform 3 (2003)], and FIG. 22 shows the histogram thereof. In such a case, the existence of the change of the waveform cannot be determined by the skewness or kurtosis.

In order to judge a difference between the waveform such as the waveform 3 (2003) and the waveform 2 (1803) shown in FIG. 19, a range (range between maximum and minimum) of the intensity change of the waveform may be focused. However, a case that the variation itself becomes a large intensity range is conceivable, and therefore, the existence of the change cannot be judged by focusing only on an absolute value of the range. Accordingly, the change is quantified by a ratio of the range and the variation.

With reference to FIG. 23, the quantification of the change by the ratio of the range and the variation will be explained.

When a waveform 3 (2203) is a sampled waveform (whose data is z(t): a symbol "t" is a time point), the waveform is obtained by adding the variation to a smoothed waveform f(t) 2207. The variation range is a difference between the maximum variation 2204 which is an upper envelope of the waveform and the minimum variation 2205 which is a lower envelope thereof.

Accordingly, the variation range is set to 6σ (σ is a standard deviation). The 6σ is a range satisfying almost all the data in which only about 3 among 1000 pieces of data (probability of 1% or lower) deviate from this range. Also, when the number of pieces of data is several tens or more, the σ is stably calculated, and therefore, this is appropriate as a definition of the range. This assumption can be expressed by the following equation (9).

[Formula 4]

$$\max(z) - \min(z) = \max f(t) - \min f(t) + 6\sigma \quad (9)$$

Here, a symbol "max" represents the maximum value, and a symbol "min" represents the minimum value.

In order to obtain the variation σ, two continuous optical emission intensities are focused. Note that, in consideration of realistic waveform characteristics, it is assumed that the change "$\Delta f(t) = f(t+\Delta t) - f(t)$" of the smoothed waveform f(t) 2207 in a continuous time interval is smaller than the variation σ.

A relation between the variation σ and a variance of a difference between two continuous intensities z(t) and z(t+Δt) is obtained as expressed by the following equation (10).

[Formula 5]

$$E(z(t) - z(t+\Delta t))^2 = 2\sigma^2 + E(\Delta f(t))^2 = 2\sigma^2 \quad (10)$$

Here, a symbol "E" means an expected value of a variable.

By substituting the σ of the equation (10) into the equation (9) and transforming the equation, the following equation (11) is obtained.

[Formula 6]

$$\sqrt{2} \frac{\max(z) - \min(z) - (\max f(t) - \min f(t))}{\sqrt{E(z(t) - z(t+\Delta t))^2}} = 6 \quad (11)$$

Accordingly, an index of quantifying the existence of the change is defined by the following expression (12).

[Formula 7]

$$\sqrt{2} \frac{\max(z) - \min(z)}{\sqrt{E(z(t) - z(t+\Delta t))^2}} \quad (12)$$

This index is called a variation index. If there is no change in the waveform, that is, if the smoothed waveform f(t) is almost constant, the variation index is about 6. If there is the change, the variation index has a larger value than 6. In calculation of the variation index, only the sampled optical emission intensity is used.

As described above, the existence of the waveform change can be judged by the skewness, the kurtosis, and the variation index. In any of the cases, an upper limit and a lower limit are set, and, if all of them are within a range between the upper limit and the lower limit, it is determined that there is no change in the waveform. For example, the upper limits of the skewness and the kurtosis are set to 1, the lower limits thereof are set to −1, the upper limit of the variation index is set to 8, and the lower limit thereof is set to 4.

According to an example of waveforms shown in FIG. 24, it is determined that a waveform (1) 2301 has the waveform change because the variation index exceeds the upper limit, and a waveform (2) 2311 has the waveform change because the skewness exceeds the lower limit and both of the kurtosis and the variation index exceed the upper limits.

On the other hand, it can be determined that a waveform (3) 2321 and a waveform (4) 2331 have no waveform change because all of the skewness, the kurtosis, and the variation index are within the ranges of the upper limits and the lower limits.

Note that the range of the waveform for obtaining the skewness, the kurtosis, and the variation index may be a range of the entire etching treatment time or a range at a certain specific time point.

Figure 25:
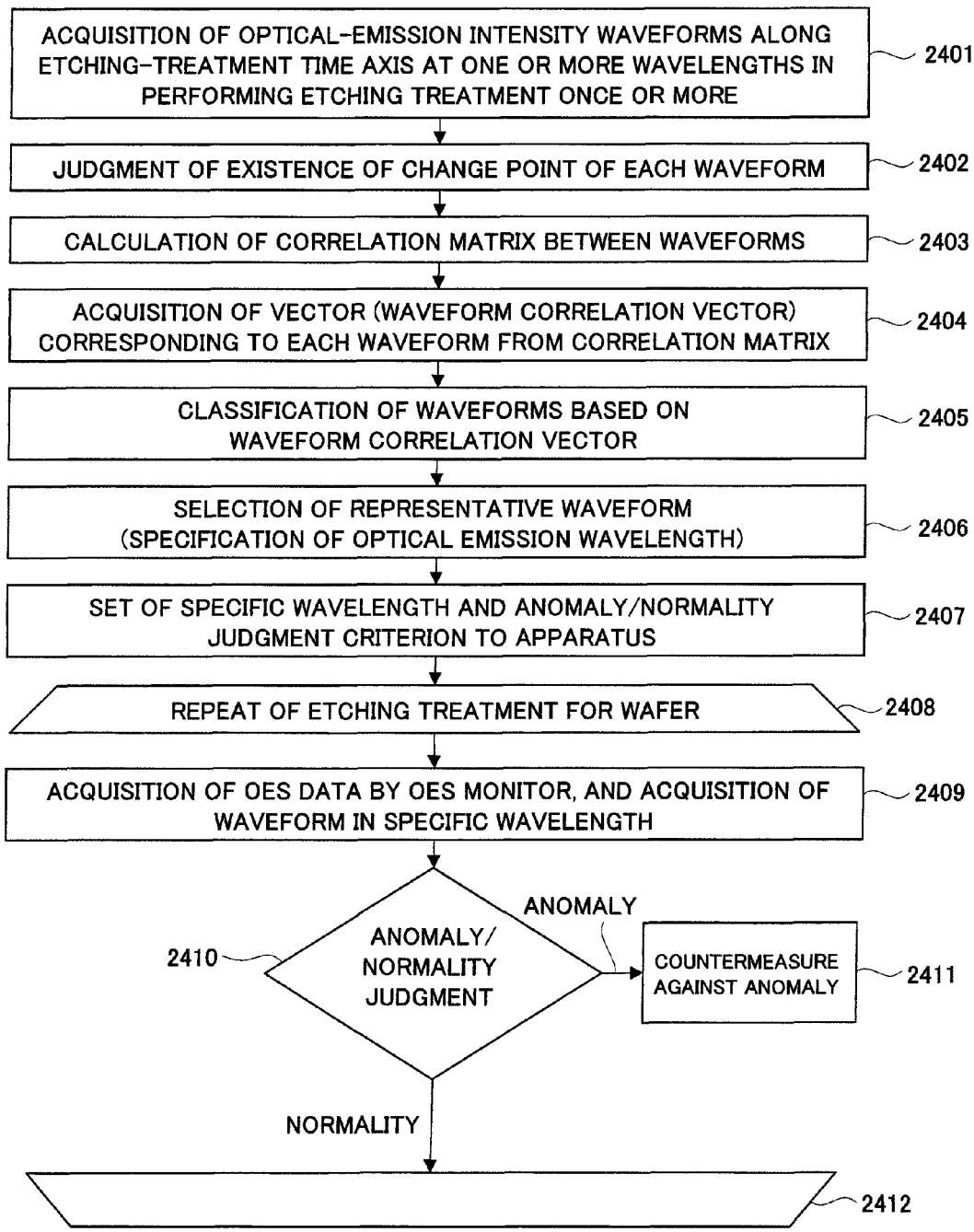
FIG. 25 is a flowchart showing an etching treatment method in the etching apparatus according to the embodiment of the present invention.
Figure 26:
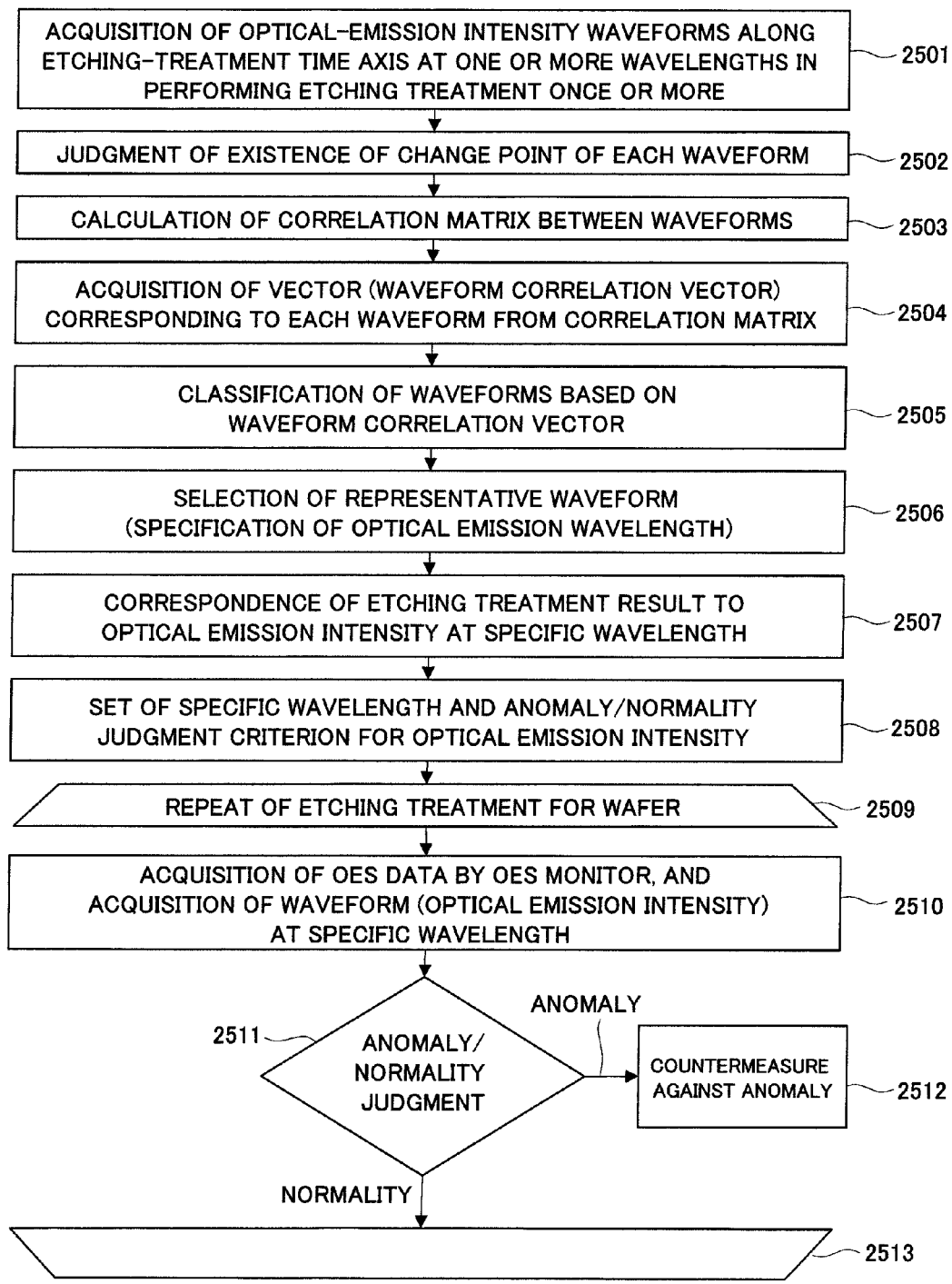
FIG. 26 is a flowchart showing another etching treatment method in the etching apparatus according to the embodiment of the present invention.

Next, with reference to FIGS. 25 and 26, an etching apparatus of automatically determining the wavelength to be monitored with using the waveform correlation cluster analysis and the determination of the existence of the waveform change described above, and an etching treatment method of monitoring the etching treatment with corresponding to the etching treatment result will be explained. FIGS. 25 and 26 are flowcharts showing the etching treatment method of the etching apparatus according to the embodiment of the present invention, FIG. 25 shows the etching treatment method in the etching apparatus of automatically judging the wavelength to be monitored, FIG. 26 shows the etching treatment method of automatically judging the wavelength to be monitored and monitoring the wavelength with corresponding to the etching treatment result, and these are an example of the anomaly/normality judgment of the etching treatment in the etching apparatus.

First, it is assumed that the OES data obtained by already performing the etching treatment once or more is stored in the calculator/storage device of the apparatus.

In the etching treatment method of the etching apparatus of automatically judging the wavelength to be monitored, as shown in FIG. 25, the waveform(s) at one or more wavelengths in performing the etching treatment once or more are acquired (step 2401). That is, this is a process of extracting the data from the storage device by the calculator of the etching apparatus.

And, the existence of the change of the acquired waveform is judged (step 2402). In the judgment, for example, the skewness, the kurtosis, and the variation index described above may be used. If it is judged that the waveform does not have any change, the wavelength of the waveform is eliminated from the monitored target since the wavelength of the waveform is caused from the substance not affecting the etching. However, if it is aimed to always monitor the no waveform change in the etching treatment, the wavelength is the monitored target.

And, with taking the waveform having the change as the target, a correlation matrix between the waveforms is calculated (step 2403). With setting each column or each row of the obtained correlation matrix to the vector, the waveform correlation vector corresponding to each waveform is acquired (step 2404).

And, based on the waveform correlation vector for each waveform, the waveforms are classified (step 2405). For the classification, for example, the above-described cluster analysis may be used, or the k-means method or the self-organization map may be used.

And, the representative waveform is selected, and the wavelength of the waveform is specified (step 2406). For the selection of the representative waveform, for example, as described above, the maximum value of the average value of the correlation coefficients between the waveforms classified into the same group, the minimum value or the maximum value of the correlation coefficient, or others may be used. In this manner, the wavelength to be monitored is determined. In the case of classifying the waveforms at the same wavelength in the plurality of etching treatments, the treatment having the waveform change is classified.

In order to judge the anomaly/normality of the etching treatment, it is required to determine the judgment criterion of this, an average or a variation of the plurality of waveforms at the same wavelength is used, and the criterion may be automatically determined so that, for example, a range of an average ±3σ is set as the normality. Alternatively, the criterion is arbitrarily manually determined. If the waveforms are classified in the plurality of etching treatments at the same wavelength, the criterion is determined based on the difference in the optical emission intensity between the groups. Instead of the criterion of the optical emission intensity, the value of the correlation coefficient based on the reference waveform may be the criterion.

And, the wavelength and the criterion of the anomaly/normality judgment specified in step 2406 are set in the etching apparatus (step 2407). In the case of using the correlation coefficient of the waveform, the reference waveform is also set.

Hereinafter, in repetitive steps 2408 to 2412 for the etching treatment of the wafer, the anomaly/normality is automatically judged.

The etching treatment is performed, the OES data is acquired by an OES monitor, and the waveform at the wavelength set in the step 2407 is acquired (step 2409).

And, the judgment is made based on the criterion of the anomaly/normality judgment set in the step 2407 (step 2410).

If the anomaly is judged in the step 2410, a countermeasure against the anomaly is performed (step 2411). For example, the countermeasure is a process of automatically stopping the treatment or interlocking in the etching apparatus or an operation of notifying the anomaly to an operator or others for replacing parts or correcting conditions.

If the normality is judged in the step 2410, the treatments of the steps 2408 to 2412 are repeated.

In order to analyze/evaluate the etching treatment result with corresponding to the etching treatment result, it is not particularly required to set the criterion of the anomaly/normality judgment in the step 2407. The waveform acquired in the step 2409 may be stored in the storage device, the measurement result of the etching treatment result by the inspection device may be acquired in the etching apparatus, and the regression analysis may be performed to the relation between the optical emission intensity and the etching treatment result. Also, the reference waveform may be set, and the regression analysis is performed to the relation between the etching treatment result and the correlation coefficient between the waveform and an obtained waveform.

Further, in order to improve the accuracy of the etching treatment result, the waveform and the etching treatment condition in the etching treatment are stored in the storage device in the step 2409, the etching treatment result which is the inspection result is acquired for the etching apparatus, and besides, a target value of the etching treatment result is acquired, and the etching treatment condition is corrected from the difference between the inspected etching treatment result and the target value by referencing the optical emission intensity of the waveform. The corrected treatment condition may be employed as a treatment condition in a next etching treatment.

Note that, if the relation between the etching treatment result and the optical emission intensity is determined by an equation such as APC (Advanced Process Control) with VM (Virtual Metrology), the treatment result can be directly estimated from the optical emission intensity, and the etching treatment condition can be corrected from the difference from the target value of the etching treatment result. As the method of using the waveform, the correlation coefficient with not only the optical emission intensity but also the reference waveform may be used. Note that the estimation of the inspection result from the data obtained from the apparatus during the treatment is called VM (Virtual Metrology).

Also, even if the analysis apparatus for the plasma emission is configured to be mounted on the etching apparatus, the similar treatment can be achieved by communicating information via an external controller.

Next, as shown in FIG. 26, as the etching treatment method of automatically determining the wavelength to be monitored and monitoring the etching treatment with corresponding to the etching treatment result, first, it is assumed that the OES data obtained in already performing the etching treatment once or more is stored in the database 433. The OES data analysis system 434 acquires the waveform at one or more wavelengths in performing the etching treatment once or more (step 2501).

And, the existence of the change of the acquired waveform is determined (step 2502). For the judgment, for example, the above-described skewness, the kurtosis, and the variation index may be used.

And, with taking the waveform having the change as the target, the correlation matrix between the waveforms is calculated (step 2503). With setting each column or each row of the obtained correlation matrix as the vector, the waveform correlation vector corresponding to each waveform is acquired (step 2504).

And, the waveforms are classified based on the waveform correlation vector for each waveform (step 2505). For the classification, for example, the above-described cluster analysis may be used, or the k-means method or the self-organization map may be used.

And, the representative waveform is selected, and the wavelength of the waveform is specified (step 2506). For the selection of the representative waveform, for example, as described above, the maximum value of the average values of the correlation coefficients between the waveforms classified into the same group, the minimum value or the maximum value of the correlation coefficient, or others may be used. In this manner, the wavelength to be monitored is judged. In the case of classifying the waveforms at the same wavelength in the plurality of etching treatments, the treatment having the waveform change is classified.

And, the optical emission intensity at the wavelength specified in the step 2506 and the etching treatment result are corresponded with each other (step 2507).

Note that it is assumed that the etching treatment result measured by the inspection result is stored in the database 433. As the relation between the optical emission intensity and the etching treatment result, they may be corresponded with each other by using the statistical analysis such as the regression analysis. If it is the relation with the pass/failure of the etching treatment result, for example, discriminant analysis, average/distribution test, neural network, or SVM (Support Vector Machine) can be also used. The reference waveform may be determined, and the correlation coefficient with the waveform and the etching treatment result may be corresponded with each other. Based on the pass/failure of the etching treatment result, the criterion of the optical emission intensity or the correlation coefficient can be determined.

And, the wavelength and the criterion of the anomaly/normality judgment specified in the step 2506 are set (step 2508). In the case of using the correlation coefficient between the waveforms, the reference waveform is also set. For the setting, if it is required to judge the anomaly/normality by the etching apparatus, they are set in the etching apparatus. If it is required to judge the anomaly/normality by not the etching apparatus 401 but by using the OES data analysis system 434 in a system environment via a network, they are set in the OES data analysis system 434. The judgment criterion may be set for the waveform itself or for the etching treatment result with utilizing VM (Virtual Metrology).

Hereinafter, in repetitive steps 2509 to 2513 for the etching treatment of the wafer, the anomaly/normality is automatically judged.

The etching treatment is performed, the OES data is acquired by the OES monitor, and the waveform at the wavelength set in the step 2508 is acquired (step 2510). If the anomaly/normality is judged by the OES data analysis system, it is required to store the waveform in the database so that the waveform can be acquired by the system.

And, the judgment is made based on the criterion of the anomaly/normality judgment set in the step 2508 (step 2511). In the case of utilizing VM (Virtual Metrology), the judgment is made after estimating etching result from the obtained waveform.

If the anomaly is judged in the step 2511, a countermeasure against the anomaly is performed (step 2512).

If the normality is judged in the step 2511, the processes of steps 2409 to 2513 are repeated.

Note that, if the criterion of the anomaly/normality judgment is determined by only the waveform without corresponding to the etching treatment result, the step 2507 is unnecessary. Alternatively, the step 2507 is also to analyze/evaluate the etching treatment result with corresponding to the etching treatment result. The analysis may be made not automatically but manually.

Also, in order to improve the accuracy of the etching treatment result, in the step 2510, the waveform and the etching treatment condition in the etching treatment are stored in the database 433, and the etching treatment result which is the inspection result is also stored in the database 433.

In the OES data analysis system 434, the target value of the etching treatment result is acquired, and the etching treatment condition is corrected by referencing the optical emission intensity of the waveform from the difference between the target value and the inspected etching treatment result. The corrected treatment condition may be used as a treatment condition in a next etching treatment.

Note that, if the relation between the etching treatment result and the optical emission intensity is determined by an equation such as APC (Advanced Process Control) with VM (Virtual Metrology), the treatment result can be directly estimated from the optical emission intensity, and the etching treatment condition can be corrected from the difference from the target value of the etching treatment result. As the method of using the waveform, the correlation coefficient with not only the optical emission intensity but also the waveform may be used.

As described above, in the present embodiment, the intensity of the change of the waveform of the OES data can be quantified, and the existence of the change can be judged, and therefore, for example, the wavelength at which the amount of the substance is not changed inside the chamber because of no contribution to the etching reaction can be specified. Alternatively, the wavelength of the optical emission at which the amount of the substance is largely changed because of largely affecting the etching reaction can be specified. In this manner, the wavelength for the end point detection can be selected.

Further, the representative wavelength can be selected from the waveforms at the plurality of wavelengths, and therefore, for example, the relation can be evaluated/analyzed with limiting the wavelength affecting the etching treatment result which is, for example, a dimension of an LSI such as a gate dimension, a step height, a circuit line width, and an aspect ratio (taper shape), characteristics such as an LER (Line Edge Roughness) and an LWR (Line Width Roughness), quantity of contamination, the number of defective chips, an etching rate, or an etching amount. Still further, the number of the pieces of sampled data for the etching can be reduced by limiting the wavelength of the optical emission, and therefore, the man-hours for obtaining the condition of the etching can be reduced.

Still further, in the start up of the etching apparatus, by previously classifying the past waveforms of the OES data in the same-type apparatus, it can be judged whether a predetermined reaction is generated or not, so that the start up can be efficient. Still further, the optical emission wavelength to be monitored can be selected, and therefore, the anomaly/normality judgment can be efficiently prepared.

In the high-volume manufacturing, the OES data can be acquired every start of work for the wafer, and therefore, the anomaly can be detected every start of work based on the shape of the waveform, that is, based on the difference in the reaction manner.

Also in maintenance, the pass/failure of the setting can be judged by the representative wavelength, and besides, can be judged based on the waveform, and therefore, the performance can be efficiently confirmed with high accuracy.

In the classification of the waveforms, with using the correlation matrix between the waveforms, the classification process is performed based on the similarity judgment by the row or column vector of the correlation matrix expressing the similarity relation between the waveforms, so that the classification by the similarity in the "shape" between the waveforms is possible. The overall similarities and the partial similarities can be collectively evaluated, and the etching treatment time range is not limited. Since the waveform "shape" is evaluated, the information about the substances and the information about the chemical reaction are unnecessary in the present classification process.

Also, in the plurality of etching treatments, by monitoring the etching treatments with using the correlation coefficient between the waveforms, the anomaly or the normality can be judged.

Further, in the plurality of etching treatments, by classifying a plurality of waveforms at the same wavelength based on the similarity, the etching treatment causing the difference in performing the etching treatment a plurality of times can be judged.

When the etching treatment is repeated with taking the waveform at the specific wavelength in a certain etching treatment as the criterion, by evaluating the correlation coefficient between the waveform at the same wavelength and the reference waveform, the change of the waveform can be quantified. By the correlation coefficient, the anomaly or the normality can be judged, the etching treatment result can be analyzed/evaluated, and the etching treatment condition can be corrected. Besides, by modeling the relation with the etching treatment result, the etching treatment result can be estimated by the correlation coefficient.

In the foregoing, the invention made by the inventors of the present invention has been concretely described based on the embodiments. However, it is needless to say that the present invention is not limited to the foregoing embodiments and various modifications and alterations can be made within the scope of the present invention.

Industrial Applicability

The present invention relates to an etching apparatus and an analysis apparatus which monitors plasma emission in the etching apparatus, and can be widely applied to an apparatus or a system which includes means for acquiring a plurality of signals during a process treatment even if the process is not the etching or even if a target of the process is not a wafer or a semiconductor device, which includes a calculator for processing the signals, and which monitors the process.

Symbol Explanation

101, 102, and 103 . . . bit map of optical emission spectrum, 104 . . . time, 105 . . . wavelength, 106 . . . gauge for optical emission intensity, 107 . . . change time point of etching treatment content, 111 . . . optical-emission spectrum distribution, 121 and 122 . . . waveform, 201 . . . first-order reaction, 202 . . . first-order reaction formula, 203 . . . second-order reaction, 204 . . . second-order reaction formula, 205 . . . high-order reaction, 206 . . . high-order reaction formula, 211 . . . chemical reaction formula, 221 . . . time, 222 . . . optical emission intensity, 231, 232, and 233 . . . waveform, 301 . . . time, 302 . . . intensity, 311, 312, 313, 314, 315, 316, and 317 . . . waveform, 401 . . . etching apparatus, 402 . . . chamber, 403 . . . electrode, 404 . . . plasma, 405 . . . wafer, 406 . . . electrode, 407 . . . exhaust system, 408 . . . gas supply system, 409 . . . apparatus controller/external communication device, 410 . . . optical emission spectrometry (OES), 411 . . . calculator/storage device, 412 . . . screen/user interface, 421 . . . window, 422 . . . light, 431 . . . inspection device, 432 . . . network, 433 . . . database (DB), 434 . . . OES data analysis system, 511 . . . lot/wafer/step-depending OES-data searching/acquiring function, 512 . . . lot/wafer/step-depending inspection-result searching/acquiring function, 521 . . . waveform-change-existence judgment function, 522 . . . waveform-correlation-matrix calculating function, 523 . . . waveform classifying function, 524 . . . representative-waveform selecting function, 525 . . . regression analysis function, 526 . . . etching-treatment-result predicting function, 527 . . . anomaly/normality judgment function, 528 . . . etching-condition correcting function, 601 . . . time, 602 . . . intensity, 611, 612, 613, and 614 . . . waveform, 621, 622, 623, and 624 . . . waveform correlation vector, 631 . . . correlation matrix, 641 . . . waveform graph, 642 . . . time, 643 . . . intensity, 651 . . . correlation matrix of waveform, 652, 653, and 654 . . . waveform correlation vector, 701 . . . cluster analysis result (dendrogram), 702 . . . group 1, 703 . . . group 2, 710 . . . distance evaluation 1, 720 . . . integration 1, 721 . . . cluster, 722 . . . gravity center, 730 . . . distance evaluation 2, 731 . . . cluster, 732 . . . gravity center, 740 . . . integration 2, 741 . . . cluster, 742 . . . gravity center of previous cluster, 743 . . . gravity center, 750 . . . distance evaluation 3, 751 . . . cluster, 752 . . . gravity center, 760 . . . integration 3, 761 . . . cluster, 762 . . . gravity center, 801 . . . waveform graph, 901 . . . waveform correlation matrix, 1001 . . . dendrogram, 1002, 1003, and 1004 . . . branch position, 1101, 1102, and 1103 . . . correlation matrix of waveform, 1111, 1112, and 1113 . . . average of correlation coefficient, 1121, 1122, and 1123 . . . representative waveform, 1201 . . . waveform graph at selected three wavelengths, 1202 . . . time, 1203 . . . intensity, 1211, 1212, and 1213 . . . waveform, 1301 . . . change graph at the same wavelength for each etching treatment, 1302 . . . time, 1303 . . . intensity, 1311 and 1312 . . . waveform, 1401 . . . waveform correlation matrix, 1501 . . . dendrogram, 1502 and 1503 . . . branch position, 1601 . . . change graph at the same wavelength for each etching treatment, 1602 . . . time, 1603 . . . intensity, 1611 and 1612 . . . waveform, 1631 . . . judgment time point, 1632 . . . intensity judgment criterion, 1701 . . . optical emission intensity change for each etching treatment, 1711 . . . correlation coefficient change for each etching treatment, 1721 . . . CD bias change for each etching treatment, 1702, 1712, and 1722 . . . etching treatment (order of start of work), 1703 . . . intensity, 1713 . . . correlation coefficient, 1723 . . . CD bias, 1801 and 1811 . . . time, 1802 and 1812 . . . intensity, 1803 and 1813 . . . waveform, 1901 . . . intensity, 1902 . . . frequency of generating data, 1911 . . . distribution of waveform 1, 1912 . . . distribution of waveform 2, 1921 . . . intensity average of waveform 1, 1922 . . . intensity average of waveform 2, 2001 . . . time, 2002 . . . intensity, 2003 . . . waveform, 2004 . . . range, 2101 . . . intensity, 2102 . . . frequency of generating data, 2103 . . . distribution of waveform 3, 2104 . . . average of waveform 3, 2301, 2311, 2321, and 2331 . . . waveform graph and skewness, kurtosis, and variation index, 2302, 2312, 2322, and 2332 . . . time, 2303, 2313, 2323, and 2333 . . . intensity

The invention claimed is:

1. An etching apparatus comprising:
a chamber configured to enclose a plasma etching treatment;
an electrode configured to generate plasma;
a gas supply/exhaust system;
a spectrometer configured to monitor optical emission of the plasma; and
a calculator system configured to process a signal monitored by the spectrometer, and configured to display, on a terminal, a result of a processing,
the calculator system including:
an optical-emission-intensity waveform acquiring unit configured to acquire a plurality of optical-emission-intensity waveforms along an etching-treatment time axis, in plasma emission data obtained during one or more etching treatments;
a waveform-change-existence judging unit configured to determine an existence, or lack thereof, of change amongst the plurality of optical emission intensity waveforms acquired by the optical-emission-intensity waveform acquiring unit;
a waveform-correlation-matrix calculating unit configured to calculate a correlation matrix between the optical emission intensity waveforms determined to have changed by the waveform-change-existence judging unit;
a waveform classifying unit configured to set each column or each row of the correlation matrix calculated by the waveform-correlation-matrix calculating unit to be a vector corresponding to an optical emission intensity waveform, configured to evaluate a similarity between optical emission intensity waveforms, based on values of the vectors, and configured to classify the optical emission intensity waveforms into groups; and a representative-waveform selecting unit configured to select a representative optical emission intensity waveform from a group classified by the waveform classifying unit, configured to specify the selected representative optical emission intensity waveform as an optical emission intensity waveform affecting performance of etching on a wafer or treatment result of etching on a wafer, configured to determine a wavelength at which the optical emission intensity waveform is obtained as an optical emission wavelength to be monitored, and configured to display a determination result on the terminal.

2. The etching apparatus according to claim 1, wherein the optical emission intensity waveform acquired by the optical-emission-intensity waveform acquiring unit is an optical emission intensity waveform with a plurality of wavelengths which are arbitrarily specified.

3. The etching apparatus according to claim 1, wherein the optical emission intensity waveform acquired by the optical-emission-intensity waveform acquiring unit is a waveform at a wavelength which peaks on an optical emission spectrum.

4. The etching apparatus according to claim 1, wherein the optical emission intensity waveform acquired by the optical-emission-intensity waveform acquiring unit is an optical emission intensity waveform at the same wavelength in the one or more etching treatments.

5. The etching apparatus according to claim 1, wherein the waveform classifying unit is configured to evaluate the similarity between optical emission intensity waveforms, based on values of the vectors, by using: cluster analysis, a k-means method, or a self-organization map.

6. The etching apparatus according to claim 1, wherein for an intensity of the optical emission intensity waveform, the waveform-change-existence judging unit is configured to obtain values of a skewness, a kurtosis, and an intensity change range with respect to variation of the intensity, and to determine whether or not the intensity is changed during etching treatment, based on the obtained values of the skewness, the kurtosis, and the intensity change range with respect to the variation of the intensity.

7. The etching apparatus according to claim 6, wherein the variation is a square of root-mean-square of a difference between continuous intensities of the optical emission intensity waveform,
the intensity change range is a difference between the maximum value and the minimum value of the intensities of the optical emission intensity waveform, and
the value of the intensity change range with respect to the variation is a value obtained by dividing the intensity change range by the variation and multiplying the divided value by square root of 2.

8. The etching apparatus according to claim 6, wherein the waveform-change-existence judging unit is configured to determine that the optical emission intensity waveform is white noise and has no intensity change, when
the skewness has a value in the range between −1.0 to 1.0, inclusive,
the kurtosis has a value in the range between −1.0 to 1.0, inclusive, and
the value of the intensity change range with respect to the variation is between 4 to 8, inclusive.

9. An analysis apparatus comprising:
a spectrometer configured to monitor optical emission of plasma; and
a calculator system configured to process a signal monitored by the spectrometer, and configured to display, on a terminal, a result of a processing,
the calculator system including:
optical-emission-intensity waveform acquiring unit configured to acquire a plurality of optical-emission-intensity waveforms along an etching-treatment time axis, in plasma emission data obtained during one or more etching treatments;
a waveform-change-existence judging unit configured to determine an existence, or lack thereof, of change amongst the plurality of optical emission intensity waveforms acquired by the optical-emission-intensity waveform acquiring unit;
a waveform-correlation-matrix calculating unit configured to calculate a correlation matrix between the optical emission intensity waveforms determined to have changed by the waveform-change-existence judging unit;
a waveform classifying unit configured to set each column or each row of the correlation matrix calculated by the waveform-correlation-matrix calculating unit to be a vector corresponding to an optical emission intensity waveform, configured to evaluate a similarity between optical emission intensity waveforms, based on values of the vectors, and configured to classify the optical emission intensity waveforms into groups; and
a representative-waveform selecting unit configured to select a representative optical emission intensity waveform from a group classified by the waveform classifying unit, configured to specify the selected representative optical emission intensity waveform as an optical emission intensity waveform affecting performance of etching on a wafer or treatment result of etching on a wafer, configured to determine a wavelength at which the optical emission intensity waveform is obtained as an optical emission wavelength to be monitored, and configured to display a determination result on the terminal.

10. An etching treatment method, using a calculator system configured to control an etching apparatus or an analysis apparatus of the etching apparatus, the etching treatment method comprising:
acquiring a plurality of optical-emission-intensity waveforms along an etching-treatment time axis, in plasma emission data obtained during one or more etching treatments;
determining an existence or lack thereof of change amongst the acquired plurality of optical emission intensity waveforms;
calculating a correlation matrix between the optical emission intensity waveforms determined to have changed;
setting each column or each row of the correlation matrix to be a vector corresponding to an optical emission intensity waveform;
evaluating a similarity between optical emission intensity waveforms, based on values of the vectors;
classifying the optical emission intensity waveforms into groups;
selecting a representative optical emission intensity waveform from a group classified by waveform classifying unit, corresponding an etching treatment to an optical emission intensity at a wavelength of the selected representative optical emission intensity waveform; and monitoring the optical emission intensity at the wavelength of the representative optical emission intensity waveform while performing a subsequent etching treatment, by using optical emission intensity data during the etching treatment.

11. An etching treatment method, using a calculator system configured to control an etching apparatus or an analysis apparatus of the etching apparatus, the etching treatment method comprising:

acquiring, from a plurality of etching treatments, an etching treatment result and an optical-emission-intensity waveform along an etching-treatment time axis at the same wavelength in plasma emission data obtained during the etching treatments;

obtaining a correlation coefficient between the optical emission intensity waveform in an etching treatment and the optical emission intensity waveforms in all other etching treatments; and corresponding a relationship between the etching treatment result and the correlation coefficient between the optical emission intensity waveforms, and monitoring the etching treatment on a wafer based on a value of the correlation coefficient between optical emission intensity waveforms while performing the etching treatment.

12. The etching treatment method according to claim 11, wherein while monitoring the etching treatment on the wafer based on the value of the correlation coefficient, by using the calculator system, a relationship between the etching treatment result and the correlation coefficient between the optical emission intensity waveforms is modeled by an algebraic equation, and the etching treatment result is evaluated by using the correlation coefficient between the optical emission intensity waveforms obtained by the etching treatment.

13. An etching treatment program for functioning a calculator system for an etching treatment as including:

an optical-emission-intensity waveform acquiring unit configured to acquire a plurality of optical-emission-intensity waveforms along an etching-treatment time axis, in plasma emission data obtained during one or more etching treatments;

a waveform-change-existence judging unit configured to determine an existence of change amongst the plurality of optical emission intensity waveforms acquired by the optical-emission-intensity waveform acquiring unit;

a waveform-correlation-matrix calculating unit configured to calculate a correlation matrix between the optical emission intensity waveforms determined to have changed by the waveform-change-existence judging unit;

a waveform classifying unit configured to set each column or each row of the correlation matrix calculated by the waveform-correlation-matrix calculating unit to be a vector corresponding to an optical emission intensity waveform, configured to evaluate a similarity between optical emission intensity waveforms, based on values of the vectors, and configured to classify the optical emission intensity waveforms into groups; and a representative-waveform selecting unit configured to select a representative optical emission intensity waveform from a group classified by the waveform classifying unit, configured to specify the selected representative optical emission intensity waveform as an optical emission intensity waveform affecting performance of etching on a wafer or treatment result of etching on a wafer, configured to determine a wavelength at which the optical emission intensity waveform is obtained as an optical emission wavelength to be monitored, and configured to display a determination result on a terminal.

* * * * *